(12) United States Patent
Lange et al.

(10) Patent No.: US 8,063,062 B2
(45) Date of Patent: Nov. 22, 2011

(54) COMPOUNDS WITH A COMBINATION OF CANNABINOID-CB$_1$ ANTAGONISM AND ACETYLCHOLINESTERASE INHIBITION

(75) Inventors: Josephus H. M. Lange, Weesp (NL); Cornelis G. Kruse, Weesp (NL); Belal Shadid, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 986 days.

(21) Appl. No.: 11/957,948

(22) Filed: Dec. 17, 2007

(65) Prior Publication Data

US 2008/0153867 A1    Jun. 26, 2008

Related U.S. Application Data

(60) Provisional application No. 60/875,808, filed on Dec. 20, 2006.

(51) Int. Cl.
*A61K 31/473* (2006.01)
*C07D 401/12* (2006.01)
(52) U.S. Cl. .................................... 514/297; 546/105
(58) Field of Classification Search .................. 514/297; 546/105
See application file for complete search history.

(56) References Cited

FOREIGN PATENT DOCUMENTS

| WO | WO 03/007887 A2 | 1/2003 |
|---|---|---|
| WO | WO 03/063781 A2 | 8/2003 |
| WO | WO 2004/013120 A1 | 2/2004 |
| WO | WO 2005/037199 A3 | 4/2005 |
| WO | WO 2005/118553 A2 | 12/2005 |
| WO | WO 2006/061372 A2 | 6/2006 |
| WO | WO 2006/061374 A1 | 6/2006 |
| WO | WO 2006/061376 A1 | 6/2006 |

OTHER PUBLICATIONS

Lange et al., "Synthesis, Biological Properties, and Molecular Modeling Investigations of Novel 3,4-Diarylpyrazolines as Potent and Selective CB1 Cannabinoid Receptor Antagonists," Medicinal Chemistry, vol. 47, No. 3, 2004, pp. 627-643, XP001188902, ISSN.
Carlier et al., "Heterodimeric Tacrine-Based Acetylcholinesterase Inhibitors: Investigating Ligand-Peripheral Site Interactions," Medicinal Chemistry, vol. 42, No. 20, pp. 4225-4231, XP002434602 (1999).
Morphy et al., "Designed Multiple Ligands. An Emerging Drug Discovery Paradigm," Medicinal Chemistry, vol. 48, No. 21, pp. 6523-6543, XP002434603, (2005).
International Search Report and Written Opinions, both dated Mar. 13, 2008, issued in PCT/EP2007/064169 and PCT/EP2008/050181.

Consroe, "Brain Cannaboinoid Systems as Targets for the Therapy of Neurological Disorders," *Neurobiology of Disease* 5, 534-551, 545 (1998).
Keowkase et al., "Mechanism of CNS Drugs and their Combinations for Alzheimer's Disease," *Central Nervous System Agents in Medicinal Chemistry*, 2008, 8, 241-248, 241.
Griffin et al., "A Review of Cholinergic Agents in the Treatment of Neurobehavioral Deficits Following Traumatic Brain Injury," J. Neuropsychiatry Clin. Neurosci 15:1, Winter 2003, 17-26.
Pertwee, R., "Neuropharmacology and therapeutic potential of cannabinoids," Addiction Biology (2000), 5, 37-46.
Masanic et al., "Open-Label Study of Donepezil in Traumatic Brain Injury," Arch. Phys. Med. Rehabil. vol. 82, Jul. 2001.
Hikida et al, Acetylcholine enhancement in the nucleus accumbens prevents additive behaviors of cocaine and morphine, Proceedings of the National Acadamy of Sciences of the United States of America May 13, 2003, vol. 1000, No. 10, 6169-6173.
Cohen et al., "CB$_1$ receptor antagonists for the treatment of nicotine addiction," *Pharmacology, Biochemistry and Behavior* 81 (2005) 387-395.
Foll et al., "Cannabinoid CB1 Receptor Antagonists as Promising New Medications for Drug Dependence," The Journal of Pharmacology and Experimental Therapeutics, vol. 312 (2005) 875-883.
Tzavara et al., "The CB1 receptor antagonist SR141716A selectively increases monoaminergic neurotransmission in the medial prefrontal cortex: implications for therapeutic actions," British Journal of Pharmacology (2003) 138, 544-553 (2003).
Tenovuo, Cholinergic Treatment of Traumatic Brain Injury, Current Drug Therapy, 2006, 1, 187-209.

*Primary Examiner* — Charanjit Aulakh
(74) *Attorney, Agent, or Firm* — Finnegan, Henderson, Farabow, Garrett & Dunner, L.L.P.

(57) ABSTRACT

Embodiments of this invention relate to compounds having a combination of cannabinoid-CB$_1$ antagonism and cholinesterase inhibition, to pharmaceutical compositions comprising these compounds, to methods for preparing these compounds, methods for preparing novel intermediates useful for the synthesis of these compounds, and methods for preparing compositions comprising these compounds. The invention also relates to methods of treating Alzheimer's disease, cognitive disorders, memory disorders, dementia, attention deficit disorder, traumatic brain injury, drug dependence, addiction or substance abuse by administering a pharmaceutical composition comprising these compounds to a patient in need thereof. A compound with a combination of cannabinoid-CB$_1$ antagonism and cholinesterase inhibition is a compound of formula (1)

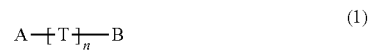

(1)

wherein the symbols have the meanings given in the specification.

11 Claims, No Drawings

COMPOUNDS WITH A COMBINATION OF CANNABINOID-CB$_1$ ANTAGONISM AND ACETYLCHOLINESTERASE INHIBITION

This application claims the benefit of priority of U.S. Provisional Application No. 60/875,808, filed on Dec. 20, 2006, the disclosure of which is incorporated herein by reference.

This invention relates to the fields of pharmaceutical and organic chemistry, and provides compounds with a combination of cannabinoid-CB$_1$ antagonism and cholinesterase inhibition, intermediates for synthesizing these compounds, formulations comprising these compounds, methods for preparing these compounds, and methods for preparing compositions comprising these compounds.

A reductionist 'one target-one disease' approach has dominated the pharmaceutical industry for some decades. Using this strategy, many successful drugs were discovered. Despite that however, many diseases remain inadequately treated. These findings rationalize an alternative approach, wherein chemical entities are developed that simultaneously modulate multiple targets. Such drugs may show advantageous properties such as increased clinical efficacy, or lack of undesired pharmacokinetic drug-drug interactions, or unfavorable pharmacokinetic and pharmacodynamic properties. The latter may lead to unpredictable variability between individual patients. In order to combine different therapeutic mechanisms, cocktails of two or more drugs are still used in clinical practice. Alternatively, multicomponent drugs are being used wherein two or more pharmaceutically active compounds are co-formulated in a single tablet or capsule in order to improve patient compliance. Another approach utilizes a pharmaceutical treatment with a chemical entity that is able to modulate more than one biological target simultaneously. It is clear that such a 'single entity-multiple target approach' offers the advantage of a lower risk of undesired drug-drug interactions compared to drug cocktails or multicomponent drugs. Several multiple target ligands are known. The majority were found retrospectively or by accident; only a few were rationally designed.

Cannabinoid receptors are part of the endo-cannabinoid system, involved in many diseases. Detailed information on cannabinoid receptors, CB$_1$ receptor modulators, and their pharmacological activities, are the subject of many recent reviews (Landsman, 1997; Lichtman, 2002; De Petrocellis, 2004; Di Marzo, 2004; Hertzog, 2004; Lange, 2004, 2005; Smith, 2005; Thakur, 2005; Padgett, 2005; Muccioli, 2005; Lambert, 2005; Vandevoorde, 2005). Potential therapeutic applications of CB$_1$ receptor modulators disclosed in the listed reviews include medicaments for treating psychosis, anxiety, depression, attention deficit disorder, memory disorders, cognitive disorders, appetite disorders, obesity, addiction, appetence, drug dependence, neurodegenerative disorders, dementia, dystonia, muscle spasticity, tremor, epilepsy, multiple sclerosis, traumatic brain injury, stroke, Parkinson's disease, Alzheimer's disease, epilepsy, Huntington's disease, Tourette's syndrome, cerebral ischaemia, cerebral apoplexy, craniocerebral trauma, spinal cord injury, neuroinflammatory disorders, plaque sclerosis, viral encephalitis, demyelinisation related disorders, as well as for the treatment of pain disorders, including neuropathic pain disorders, septic shock, glaucoma, diabetes, cancer, emesis, nausea, gastrointestinal disorders, gastric ulcers, diarrhoea, sexual disorders, impulse control disorders and cardiovascular disorders.

Cholinesterases, including acetylcholinesterase and butyrylcholinesterase, are serine hydrolases. Alzheimer's disease (AD) is a neurodegenerative disorder whose prevalence is increasing together with life expectancy throughout the world. Cholinergic-enhancing drugs are the main current therapy for Alzheimer's disease (Terry, 2003).

Tacrine (Trade name: Cognex®) was the first approved by the FDA for AD treatment. This substance, an acetylcholinesterase, as well as a butyryl-cholinesterase inhibitor, showed clinically significant improvement in cognition in AD-patients. Currently, three other AChE inhibitors are available for treating AD: donepezil (Aricept®), rivastigmine (Exelon®), and galanthamine (Reminyl®). Like donepezil and rivastigmine, tacrine is a reversible inhibitor that presumably acts centrally by elevating the acetylcholine level in the cerebral cortex, and by slowing degradation of acetylcholine from intact cholinergic neurons (Brufani, 1997; Weinstock, 1999). It has been shown that AChE inhibitors have potential in the modulation of amyloid precursor protein processing (Racchi, 2004). The structures of tacrine, amiridine, 7-methoxytacrine, and SM-10888 are closely related, whereas for example donepezil has a somewhat more elongated structure. Structures and cholinesterase inhibiting activities of compounds structurally related to tacrine were recently reviewed in Marco, 2003, but many more AChE inhibitors have been described in the (patent) literature.

Drug dependence poses serious social, medical, and economic problems. Effective treatments are still limited. Recently, it was found that AChE inhibitors that act on the brain suppressed both cocaine- and morphine-induced conditioned place preference, and blocked the induction and persistence of cocaine-evoked hyperlocomotion. Thus, centrally active AChE inhibitors are novel potential therapeutic agents for drug addiction (Hikida, 2003). Also cannabinoid CB$_1$ antagonists were suggested for treating drug addiction (Cohen, 2002; Hungund, 2002; Solinas, 2003). AChE inhibitors have shown efficacy not only in Alzheimer's disease (Spencer, 1998), but also in other cognitive disorders such as dementia with Lewy bodies (McKeith, 2000), Parkinson's disease (Werber, 2001), vascular dementia (Kumar, 2000), and traumatic brain injury (Masanic, 2001). Butyryl-cholinesterase is considered as a potential target for Alzheimer's disease because it also regulates acetylcholine levels (Darvesh, 2003).

Cognitive disorders are also a potential therapeutic area for cannabinoid CB$_1$ receptor antagonists (Castellano, 2003; Wolff, 2003). CB$_1$ receptor antagonists were shown to increase acetylcholine (Ach) release in certain brain areas including the cortical region and hippocampus (De Groot, 2006). The selective CB$_1$ receptor antagonist rimonabant showed neuroprotective activity in animal stroke models (Berger, 2004). In summary, scientific articles, patents, and patent applications indicate the following therapeutic applications for cholinesterase inhibitors: alcoholism, Alzheimers disease, amnesia, arthritis, cancer, central nervous system disease, cognitive disorder, constipation, dementia, dyspepsia, gastric motility disorder, gastrointestinal disease, gastroparesis, glaucoma, irritable bowel syndrome, major depressive disorder, migraine, multiple sclerosis, muscle disease, muscular dystrophy, myasthenia gravis, neurodegenerative disease, neuropathic pain, nicotine dependence, *Pediculus capitis* infestation, poison intoxication, postviral fatigue syndrome, psychiatric disorder, senile dementia, schistosomiasis, urinary dysfunction and xerostomia.

Because of the frequently observed co-morbidity of symptoms of different diseases, compounds combining cannabinoid-CB$_1$ antagonism with cholinesterase inhibition can be useful to treat the conditions wherein either a cannabinoid CB$_1$ antagonist or a cholinesterase inhibitor is potentially effective. Thus, the compounds of the invention can be used for treating addiction, appetence, alcoholism, Alzheimers disease, amnesia, anxiety, appetite disorders, arthritis, attention deficit disorder, cancer, cardiovascular disorders, central nervous system disease, cerebral apoplexy, cerebral ischaemia, cognitive disorder, constipation, dementia, demyelinisation related disorders, depression, diabetes, diarrhoea, drug dependence, dyspepsia, dystonia, emesis, epilepsy, gastric motility disorder, gastric ulcers, gastrointestinal disorders, gastroparesis, glaucoma, Huntington's disease, impulse control disorders, irritable bowel syndrome, memory disorders, migraine, multiple sclerosis, muscle disease, muscular dystrophy, muscle spasticity, myasthenia gravis, nausea, neurodegenerative disorders, neuroinflammatory disorders, neuropathic pain, nicotine dependence, obesity, pain disorders, Parkinson's disease, *Pediculus capitis* infestation, plaque sclerosis, poison intoxication, postviral fatigue syndrome, psychiatric disorder, psychosis, senile dementia, septic shock, sexual disorders, schistosomiasis, spinal cord injury, stroke, Tourette's syndrome, traumatic brain injury, tremor, urinary dysfunction, viral encephalitis and xerostomia.

Some embodiments of the present invention relate to the use of the compounds of the invention for treating disorders that are claimed to be treatable with cannabinoid $CB_1$ antagonists as well as with cholinesterase inhibitors. Attacking such disorders simultaneously via two different mechanisms of action can have synergistic effects. The compounds of the invention are particularly useful for treating Alzheimer's disease, cognitive disorders, memory disorders, dementia, attention deficit disorder, traumatic brain injury, drug dependence, addiction and substance abuse.

The pharmacophore of the majority of cannabinoid $CB_1$ receptor antagonists was the subject of several reviews (Lange, 2005; Reggio, 2003). Scheme 1 generally depicts the pharmacophore of cannabinoid $CB_1$ receptor antagonists.

Scheme 1: $CB_1$ receptor antagonist pharmacophore, and one of its putative key interactions with the $CB_1$ receptor

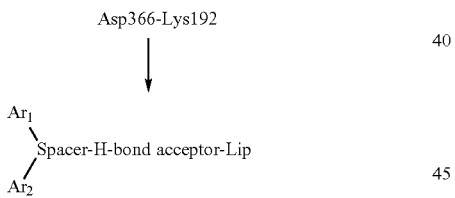

In Scheme 1, $Ar_1$ and $Ar_2$ represent phenyl groups, optionally substituted with one or two halogen atoms, trifluoromethyl groups, or methoxy groups. The 'spacer' contains a five-membered heterocyclic group such as 4,5-dihydropyrazole, imidazole, pyrazole, thiazole, thiophene, or pyrrole or the spacer contains a phenyl group or a six-membered heterocyclic group such as pyridine, pyrimidines or pyrazine. The spacer can also contain an azetidine moiety, a 1,3-benzodioxole moiety or an alkyl moiety like in MK-0364 (see below). In addition, one of the aromatic groups can be fused to the spacer, or can be connected to the spacer by an additional ring, so-called conformational constraint. Several kinds of conformational constraints have successfully been implemented in this pharmacophore model. The H-bond acceptor represents a carbonyl group, a sulfonyl group or a nitrogen-atom which might be embedded in a heterocyclic ring structure such as an imidazole ring. In Scheme 1, 'Lip' represents a lipophilic moiety, for instance piperidin-1-ylamino, pyrrolidinyl-1-amino, cycloalkylamino, phenylamino, arylamino, benzyl-amino or alkylamino.

Molecular modeling studies indicate that the presence of a hydrogen bond acceptor is crucial. It is thought that the hydrogen bond acceptor interacts with the Lys-192 amino acid residue side chain in the $CB_1$ receptor, thereby stabilizing its inactive state. To illustrate the $CB_1$ receptor antagonist pharmacophore model, a number of concrete examples of $CB_1$ receptor antagonists are depicted below. The putative hydrogen bond acceptor atom (oxygen atom from a carbonyl group, oxygen atom from a sulfonyl group, or N atom in a heteroaromatic ring) in the $CB_1$ receptor antagonists are indicated in bold:

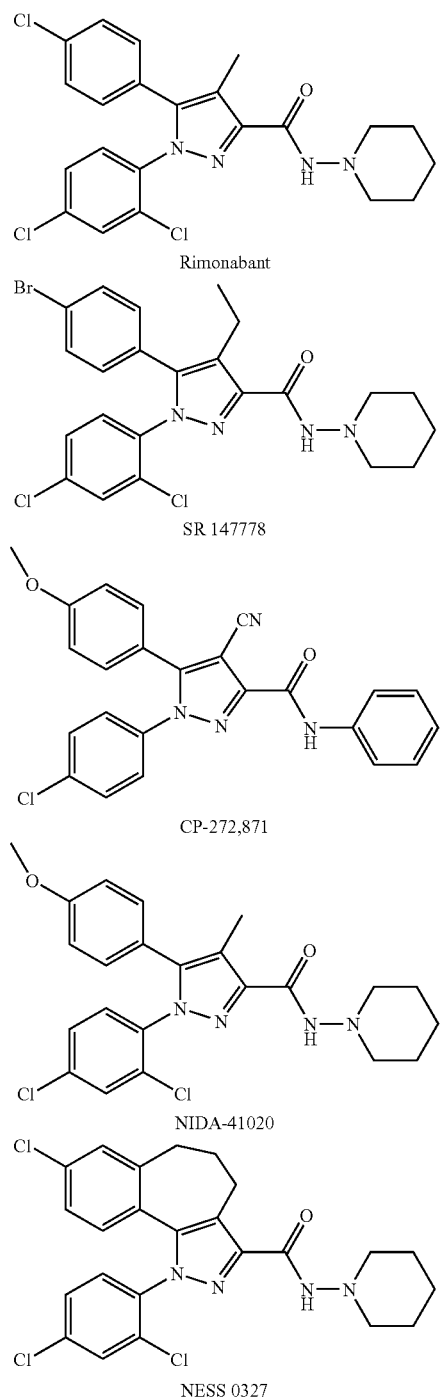

-continued
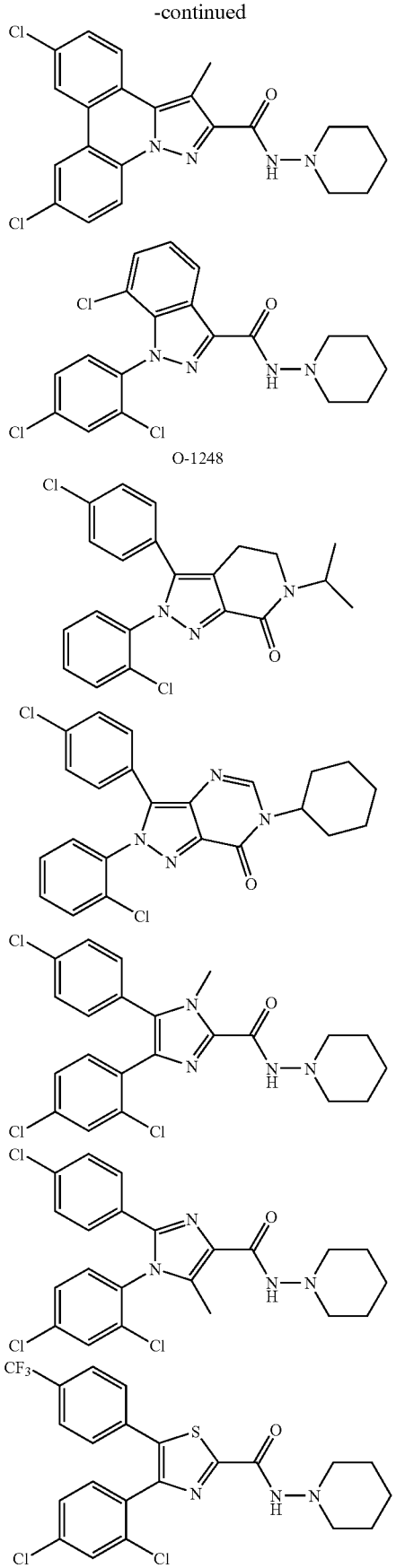
O-1248
-continued
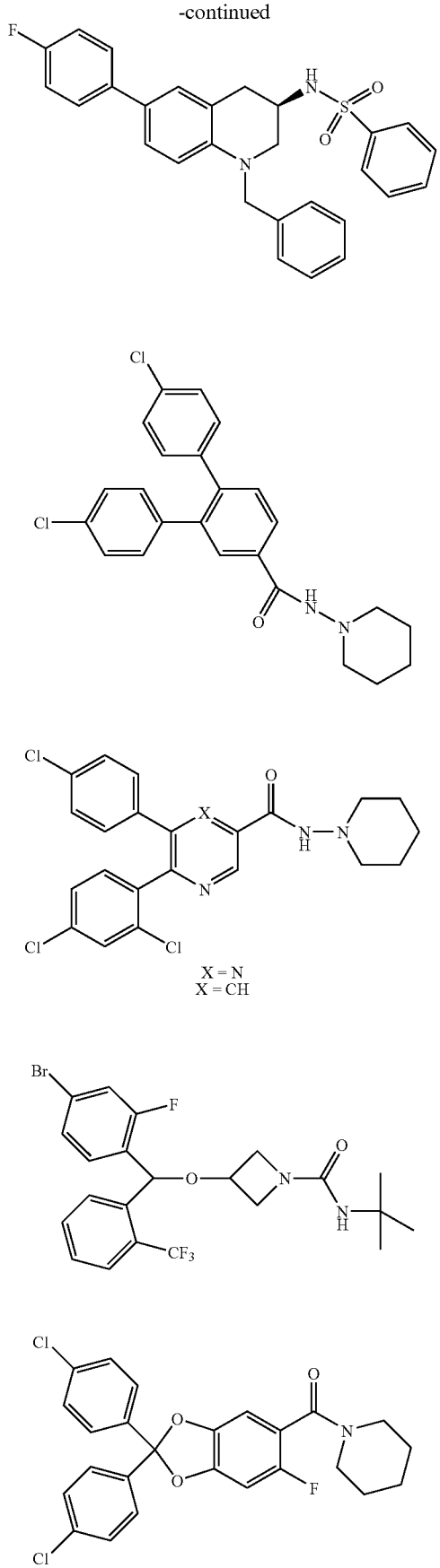
X = N
X = CH

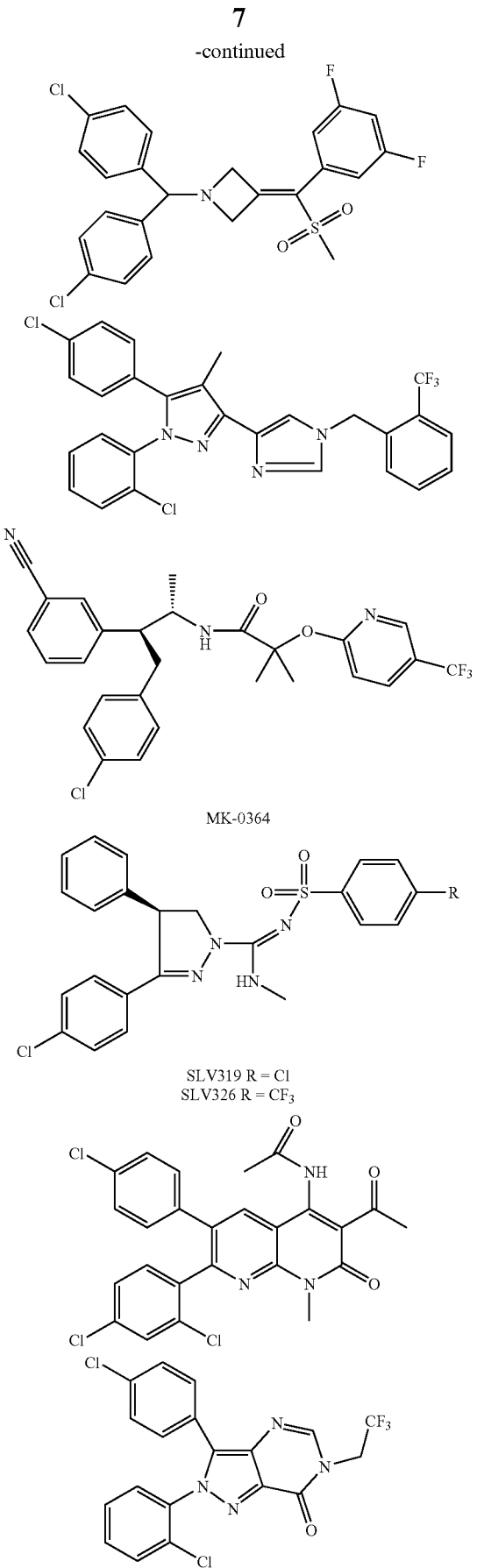
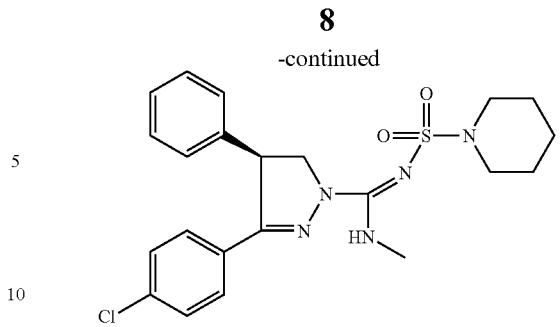

SLV319 R = Cl
SLV326 R = CF₃

MK-0364

The selective $CB_1$ receptor antagonist SR141716A (rimonabant) has been known for more than a decade. Many other selective $CB_1$ receptor antagonists were invented later. Several acetylcholinesterase inhibitors have been known for many years too. For example, tacrine was approved in the United States in 1993. Thus far, no compounds have been disclosed which exhibit a combination of $CB_1$ receptor antagonist and acetylcholinesterase inhibitor activities.

The objective of the present invention was to develop compounds with a combination of $CB_1$ antagonism and acetylcholinesterase inhibition.

DESCRIPTION OF THE INVENTION

It was found that molecules containing essential structural (activity related) components of known cannabinoid-$CB_1$ antagonists and essential structural (activity related) components of the known acetylcholinesterase inhibitor tacrine share the activity of both molecules from which they were derived: cannabinoid-$CB_1$ antagonism and inhibition of acetylcholinesterase.

Embodiments of this invention concern compounds with a combination of CB antagonism and acetyl- and/or butyrylcholinesterase inhibition. For example, embodiments of this invention comprise compounds with a combination of $CB_1$ antagonism and acetylcholinesterase inhibition.

The invention also relates, in some embodiments, to a compound of formula (1):

or a tautomer, stereoisomer, N-oxide, isotopically-labelled analogue, or a pharmacologically acceptable salt, hydrate or solvate of any of the foregoing, wherein:

A is an essential structural component of a cannabinoid-$CB_1$ antagonist comprising at least two phenyl rings, each phenyl ring is optionally substituted with one or two substituents chosen from a halogen atom, a methoxy group, and a trifluoromethyl group, said essential structural component A being connected to a carbonyl group, a sulfonyl group, or a nitrogen or oxygen atom incorporated in a heteroaromatic ring structure, T is chosen from a saturated or unsaturated linear carbon chain having from 2 to 8 carbon atoms, wherein the carbon chain is optionally substituted with from 1 to 5 substituents chosen from a methyl group, an ethyl group, a hydroxy group, a fluoro atom, and an amino group, wherein the carbon chain optionally comprises an additional nitrogen atom, optionally substituted with a $C_{1-3}$ alkyl group, or wherein the carbon chain optionally comprises an additional oxygen atom, a sulphur atom, a carbonyl group, a sulfonyl group, an amide group, a sulfonamide group, a ureido group, or an aryl group, wherein the aryl group is optionally substituted with from 1 to 4 substituents chosen from a halogen atom, a cyano group, a methyl group, a methoxy group, a trifluoromethyl group, $OCHF_2$, $OCF_3$, $SCF_3$, and a nitro group, B is an essential structural (activity related) component of any known acetylcholinesterase inhibitor, n is 0 or 1.

Other embodiments provide one or more compounds of formula (1) wherein A is an essential structural component of a $CB_1$ antagonist disclosed in any one of the following: EP1602658, EP576357, EP656354, FR2789078, FR2789079, FR2799124, FR2804604, FR2849032, FR2856683, FR2856684, FR2860792, FR2864958, FR2869905, FR2873372, FR2874012, FR2876691, FR2880023, FR2880890, FR2881744, US20040122089, US20040157838, US20040157839, US20040176418, US20040214837, US20040214855, US20040214856, US20040242593, US20040248881, US20040259887, US20040266845, US20050009870, US20050065189, US20050096379, US20050101592, US20050165012, US20050171179, US20050187208, US20050187259, US20050250769, US20050267155, US20060079556, US20060100206, US20060154955, US20060154956, US20060154958, US20060155126, US20060160850, US20060223798, U.S. Pat. No. 5,596,106, U.S. Pat. No. 6,509,367, WO9602248, WO9729079, WO9902499, WO2001029007, WO2001032629, WO2001032663, WO2001064632, WO2001064633, WO2001064634, WO2001070700, WO2001096330, WO2002076949, WO2003007887, WO2003020217, WO2003026647, WO2003026648, WO2003027069, WO2003027076, WO2003027114, WO2003040105, WO2003040107, WO2003051850, WO2003051851, WO2003063781, WO2003077847, WO2003078413, WO2003082190, WO2003082191, WO2003082833, WO2003084930, WO2003084943, WO2003086288, WO2003087037, WO2003089428, WO2004012671, WO2004013120, WO2004026301, WO2004029204, WO2004037823, WO2004048317, WO2004052864, WO2004058145, WO2004060870, WO2004060888, WO2004096763, WO2004099157, WO2004111033, WO2004111034, WO2004111038, WO2004111039, WO2005000809, WO2005009974, WO2005016286, WO2005021547, WO2005027837, WO2005044785, WO2005047285, WO2005049615, WO2005051953, WO2005061504, WO2005061505, WO2005061506, WO2005061507, WO2005063762, WO2005066126, WO2005074920, WO2005077909, WO2005080328, WO2005080343, WO2005080357, WO2005103052, WO2005115977, WO2005118553, WO2006025069, WO2006030285, WO2006041797, WO2006047516, WO2006060461, WO2006074445, WO2006080040, WO2006106054 and WO2006087732; in some embodiments, B in formula (1) is an essential structural component of a AChE inhibitor disclosed in any one of the following: DE3805744, EP1020469, EP1020470, EP141393, EP154864, EP1600447, EP298202, EP306825, EP306826, EP326106, EP354594, EP401715, EP409676, EP413667, EP415634, EP441517, EP457318, EP468401, EP471296, EP471298, EP477903, EP481429, EP487071, EP495709, EP516520, EP535496, EP567090, EP579263, EP611769, EP614888, EP627400, EP637586, EP648771, EP987262, JP02270875, JP03112989, JP04159225, JP05306286, JP07048370, JP09095483, JP09268176, RU2041878, RU2102398, US20040229914, US20050096387, US20060063769, US20060122226, US20060142335, U.S. Pat. Nos. 4,843,079, 4,868,177, 4,914,102, 4,929,731, 5,171,750, 5,185,350, 5,206,371, 5,229,401, 5,246,947, 5,264,442, 5,290,942, 5,391,553, 5,428,043, 5,547,960, 6,075,144, 6,229,014, WO2000033788, WO2000051985, WO2001016105, WO2001066096, WO2001098271, WO2003033489, WO2003082794, WO2004032929, WO2004106275, WO2005005413, WO2006039767, WO2006052496, WO2006080043, WO2006103120, WO9214710, WO9217475, WO9303034, WO9304063, WO9305779, WO9307140, WO9313083, WO9429272, WO9620176, WO9703987, WO9708146, WO9713754, WO9721681, WO9738993, WO9800412, WO9919329 and WO9964421.

Further embodiments provide one or more compounds of formula (1) wherein A is an essential structural component of the $CB_1$ antagonists: 11C-JHU-75528, A-796260, AM 251, AM 630, AVE-1625, MK-0364, CP-272871, CP-945598, GRC-10389, LY-2077855, LY-320135, NIDA-41020, O-2093, rimonabant, SLV319, SLV326, SR-140098, SR-144385, SR-147778, surinabant, V-24343, WIN-54461 and WIN-56098, and wherein B is an essential structural component of the AchE inhibitors aceclidine, ambenonium chloride, amiridine, AS-1397, BGC-20-1259, bisnorcymserine, bromodechloroambenonium, bromophenophos, BW-284-C-51, caracemide, carbofuran, CHF-2060, CHF-2822, CHF-2957, CI-1002, cisatracurium besylate, CM-2433, CM-2501, desoxypeganine, diazinon, donepezil, E-2030, edrophonium chloride, EN-101, eptastigmine, ER-127528, (−)-eseroline, F-3796, fenitrothion, FK-960, FP-7832, FR-152558, galantamine, ganstigmine, gramine, Hoe-065, HP-290, huperzine A, icopezil, INM-176, ipidacrine, isatin, isofluorophate, itopride, JES-9501, KA-672, KW-5092, ladostigil, malathion, MC1-225, mebendazole, memantine, memoquin, methanesulfonyl fluoride, N-methylphysostigmine, metrifonate, MF-268, MF-8615, MFS-3, MHP-133, mifepristone, milameline, neostigmine, nitroflurbiprofen, NP-0362, NP-7557, NXX-066, ONO-1603, P-10358, P-11012, P-11149, P-11467, P-26, paliroden, paraoxon, parathion, PD-151832, (−)-phenserine, physostigmine, pralnacasan, pramiracetam, pyridostigmine, rivanicline, rivastigmine, Ro-46-5934, RS-1439, S-9977, SDZ-ENX-792, SGS-742, SM-10888, SP-004, T-82, tacrine, 7-methoxytacrine, bis-(7)-tacrine, TAK-802, tolserine, UR-1827, velnacrine, Z-338, zanapezil, zifrosilone and ZT-1.

In another embodiment the invention relates to compounds of formula (1) wherein A is one of ($A^{1a}$), ($A^{1b}$), ($A^2$), ($A^3$) ($A^4$), ($A^5$), ($A^6$), ($A^7$), or ($A^8$):

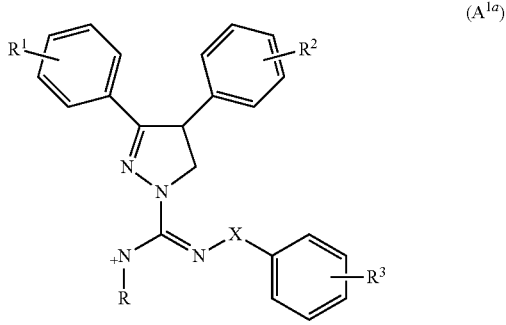

($A^{1a}$)

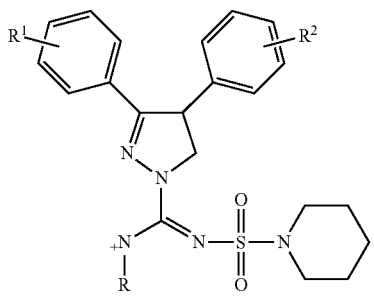
(A^{1b})

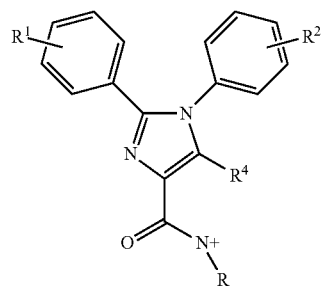
(A^2)

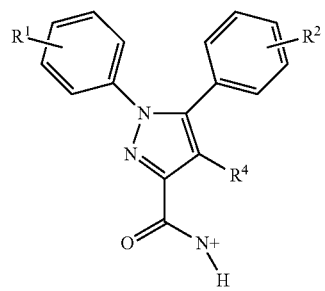
(A^3)

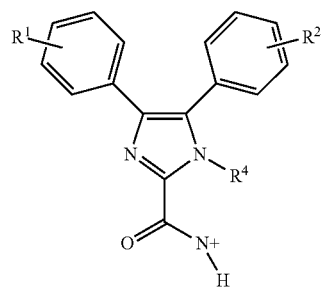
(A^4)

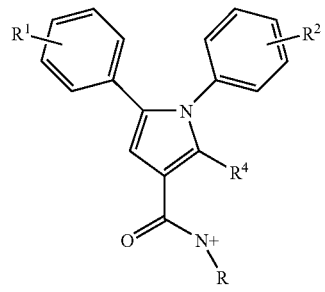
(A^5)

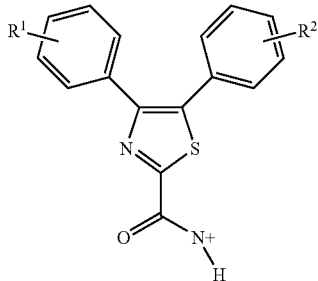
(A^6)

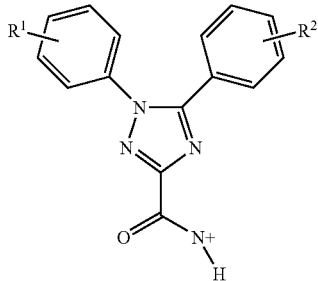
(A^7)

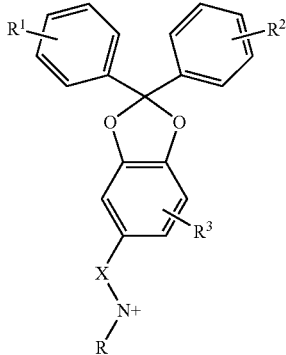
(A^8)

wherein, X is a sulfonyl or a carbonyl group, the "+" symbol is the position at which $(A^{1a})$ to $(A^8)$ is connected to T of formula (1), each of $R^1$, $R^2$ and $R^3$ is chosen from a hydrogen atom, a trifluoromethyl group and a halogen atom, $R^4$ is chosen from a hydrogen or halogen atom, a methyl group, an ethyl group, a trifluoromethyl group, a hydroxymethyl group, a fluoromethyl group, a 2,2,2-trifluoroethyl group, a propyl group, a methylsulfanyl group, a methylsulfinyl group, a methylsulfonyl group, an ethylsulfanyl group, an ethylsulfinyl group, an ethylsulfonyl group, a $C_{1-3}$-dialkyl-aminomethyl group, a pyrrolidin-1-ylmethyl group, a piperidin-1-ylmethyl group and a morpholin-4-ylmethyl group, and the other symbols have the meanings as given above.

In another embodiment, the invention relates to compounds of formula (1) in which A is one of $(A^{1a})$, $(A^{1b})$, $(A^2)$, $(A^3)$ $(A^4)$, $(A^5)$, $(A^6)$, $(A^7)$, or $(A^8)$, and B is one of $(B^1)$, $(B^2)$ or $(B^3)$:

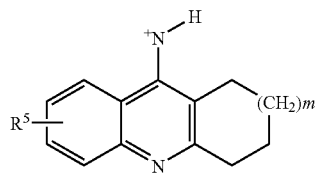
(B^1)

-continued

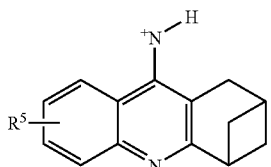
(B²)

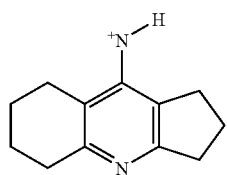
(B³)

wherein, the "+" symbol is the position at which (B¹) to (B³) is connected to T of formula (1), $R^5$ is chosen from a hydrogen atom, a halogen atom, a methoxy group, and a trifluoromethoxy group, and m is 0, 1 or 2, and the other symbols have the meanings as given above.

In another embodiment, the invention relates to compounds of formula (1) in which A is one of ($A^{1a}$), ($A^{1b}$), ($A^2$), ($A^3$) ($A^4$), ($A^5$), ($A^6$), ($A^7$), or ($A^8$), said acetylcholinesterase inhibitor B is chosen from tacrine, amiridine, 7-methoxytacrine and SM-10888, R is a hydrogen atom or a $C_{1-3}$ alkyl group, and the other symbols have the meanings as given above.

In another embodiment, the invention relates to compounds of formula (1) in which A is one of ($A^{1a}$), ($A^{1b}$) or ($A^2$), said acetylcholinesterase inhibitor B is tacrine and the other symbols have the meanings as given above.

In another embodiment, the invention relates to compounds of formula (1) in which A is one of ($A^9$) or ($A^{10}$):

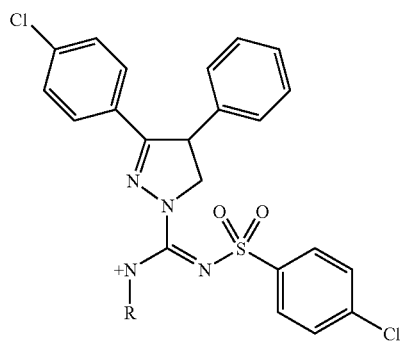
(A⁹)

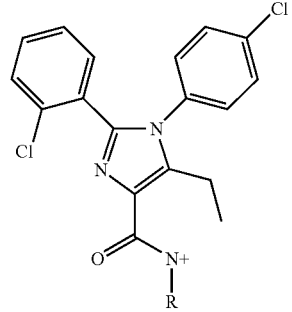
(A¹⁰)

and the other symbols have the meanings as given above.

In another embodiment, the invention relates to the compounds of formula (1), wherein the compound of formula (1) is chosen from:

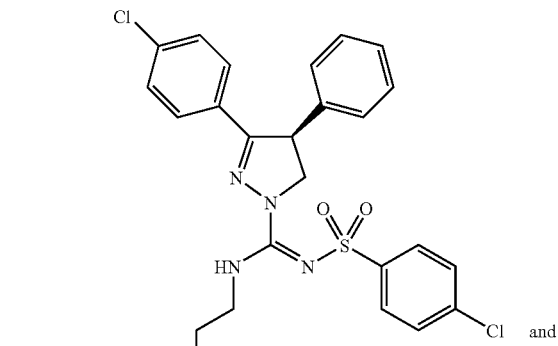
and

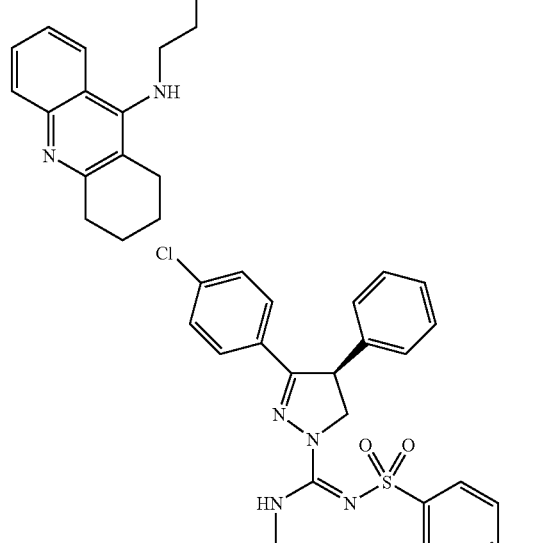

The compounds of formula (1), as well as tautomers, stereoisomers, N-oxides, isotopically-labelled analogues thereof, and pharmacologically acceptable salts, hydrates and solvates of any of the foregoing, have a combination of cannabinoid-$CB_1$ antagonism and cholinesterase inhibition, in particular acetylcholinesterase inhibition. They are useful in the treatment of disorders in which cannabinoid-$CB_1$ receptors and acetylcholinesterase sites are involved, or that can be treated via modulation of those receptors such as addiction, appetence, alcoholism, Alzheimers disease, amnesia, anxiety, appetite disorders, arthritis, attention deficit disorder, cancer, cardiovascular disorders, central nervous system disease, cerebral apoplexy, cerebral ischaemia, cognitive disorder, constipation, dementia, demyelinisation related disorders, depression, diabetes, diarrhoea, drug dependence, dyspepsia, dystonia, emesis, epilepsy, gastric motility disorder, gastric ulcers, gastrointestinal disorders, gastroparesis, glaucoma, Huntington's disease, impulse control disorders, irritable bowel syndrome, memory disorders, migraine, multiple sclerosis, muscle disease, muscular dystrophy, muscle spasticity, myasthenia gravis, nausea, neurodegenerative disorders, neuroinflammatory disorders, neuropathic pain, nicotine dependence, obesity, pain disorders, Parkinson's disease, *Pediculus capitis* infestation, plaque sclerosis, poison intoxication, postviral fatigue syndrome, psychiatric disorder, psychosis, senile dementia, septic shock, sexual disorders, schistosomiasis, spinal cord injury, stroke, Tourette's syndrome, traumatic brain injury, tremor, urinary dysfunction, viral encephalitis and xerostomia.

Other embodiments of the invention include, but are not limited to:

a pharmaceutical composition for treating, for example, a disorder or condition that may be treated by a combination of cannabinoid-$CB_1$ antagonism and acetylcholinesterase inhibition, the composition comprising a compound of formula (1), and a pharmaceutically acceptable carrier;

a method of treatment of a disorder or condition that may be treated by a combination of cannabinoid-$CB_1$ antagonism and acetylcholinesterase inhibition, the method comprising administering to a mammal in need of such treatment a compound of formula (1);

a pharmaceutical composition for treating, for example, a disorder or condition chosen from the group of disorders listed herein;

a method of treatment of a disorder or condition chosen from the group of disorders listed herein, the method comprising administering to a patient in need of such treatment a compound of formula (1);

a pharmaceutical composition for treating a disorder or condition chosen from the group of disorders listed herein, the composition comprising a compound of formula (1), and a pharmaceutically acceptable carrier;

a method for treating a disorder or condition chosen from the group of disorders listed herein, the method comprising administering to a patient in need of such treatment a compound of formula (1);

a method of antagonizing a cannabinoid-$CB_1$ antagonism receptor and inhibiting acetylcholinesterase, which comprises administering to a subject in need thereof, an effective amount of a compound of formula (1).

The invention also provides the use of a compound according to formula (1) for the manufacture of a medicament.

The invention further relates to combination therapies wherein a compound of the invention, or a pharmaceutical composition or formulation comprising a compound of the invention, is administered concurrently or sequentially or as a combined preparation with another therapeutic agent or agents, for the treatment of one or more of the conditions listed herein. Such other therapeutic agent(s) may be administered prior to, simultaneously with, or following the administration of the compounds of the invention.

The invention also provides compounds, pharmaceutical compositions, kits and methods for treating a disorder or condition chosen from the group of disorders listed herein, the method comprising administering to a patient in need of such treatment a compound of formula (1).

The compounds of the invention possess a combination of cannabinoid-$CB_1$ antagonism and cholinesterase inhibition, for example, acetylcholinesterase inhibition. The (ant)agonizing/inhibiting activities of the compounds of the invention is readily demonstrated, for example, using one or more of the assays described herein or known in the art.

The invention also provides methods of preparing the compounds of the invention and the intermediates used in those methods.

Isolation and purification of the compounds and intermediates described herein can be affected, if desired, by any suitable separation or purification procedure such as, for example, filtration, extraction, crystallization, column chromatography, thin-layer chromatography, thick-layer chromatography, preparative low or high-pressure liquid chromatography, or a combination of these procedures. Specific illustrations of suitable separation and isolation procedures can be taken from the preparations and examples. However, other equivalent separation or isolation procedures could, of course, also be used.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula (I) shows the structure of the class of compounds without preferred stereochemistry. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base, such as for example (−)-di-p-toluoyl-D-tartaric acid and/or (+)-di-p-toluoyl-L-tartaric acid. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

Cis and trans isomers of the compound of formula (1) or a pharmaceutically acceptable salt thereof are also within the scope of the invention, and this also applies to tautomers of the compounds of formula (1) or a pharmaceutically acceptable salt thereof.

Some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Isotopically-labeled compounds of formula (1) or pharmaceutically acceptable salts thereof, including compounds of formula (1) isotopically-labeled to be detectable by PET or SPECT, are also included within the scope of the invention, and same applies to compounds of formula (1) labeled with [$^{13}$C]—, [$^{14}$C]—, [$^{18}$F]—, [$^{3}$H]—, [$^{125}$I]— or other isotopically-enriched atoms, suitable for receptor binding or metabolism studies.

The compounds of the invention may also be used as reagents or standards in the biochemical study of neurological function, dysfunction, and disease.

Definitions

Within the context of this description, the terms 'compound with cannabinoid-CB$_1$ antagonism' and 'cannabinoid-CB$_1$ antagonist' refer to compounds having this activity—measured by unambiguous and well accepted pharmacological assays, including those described herein—without displaying substantial cross-reactivity towards another receptor. In one embodiment, a compound of the present invention is at least 10 times more potent as a cannabinoid-CB$_1$ antagonist than as an agonist or antagonist on any other receptor. For example, compounds with a 100-fold selectivity, or for example compounds with a selectivity of a factor 1,000 or higher. The terms 'compound with cholinesterase inhibiting activity' or 'cholinesterase inhibitor' refer to compounds having this activity—measured by unambiguous and well accepted pharmacological assays, including those described herein—without displaying substantial cross-reactivity towards another receptor. In one embodiment, a compound of the present invention is at least 10 times more potent as a cholinesterase inhibitor than as an inhibitor of any other enzyme. For example, compounds with a 100-fold selectivity, or for example compounds with a selectivity of a factor 1,000 or more. A compound 'having both cannabinoid-CB$_1$ antagonism and cholinesterase inhibiting activity' refers to compounds having both activities-measured by unambiguous and well accepted pharmacological assays, including those described herein-without displaying substantial cross-reactivity towards other receptors or enzymes. In one embodiment, a compound of the present invention is at least 10 times more potent as a cannabinoid-CB$_1$ antagonist and as a cholinesterase inhibitor than as an agonist or antagonist on any other receptor or as an inhibitor of any other enzyme. For example, compounds with a 100-fold selectivity, or for example compounds with a selectivity of a factor 1,000 or more.

General terms used in the description of compounds herein disclosed bear their usual meanings. The term alkyl as used herein denotes a univalent saturated, branched or straight, hydrocarbon chain. Unless otherwise stated, such chains can contain from 1 to 18 carbon atoms. Representative of such alkyl groups are methyl, ethyl, propyl, isopropyl, butyl, isobutyl, sec-butyl, tert-butyl, pentyl, isopentyl, neopentyl, tert-pentyl, hexyl, isohexyl, heptyl, octyl, nonyl, decyl, undecyl, dodecyl, tridecyl, tetradecyl, pentadecyl, hexadecyl, heptadecyl, octadecyl, and the like. When qualified by the term 'lower', the alkyl group will contain from 1 to 6 carbon atoms. The same carbon content applies to the parent term 'alkane', and to derivative terms such as 'alkoxy'. The carbon content of various hydrocarbon containing moieties is indicated by a prefix designating the minimum and maximum number of carbon atoms in the moiety, i.e., the prefix $C_x$-$C_y$ defines the number of carbon atoms present from the integer "x" to the integer "y" inclusive. 'Alkyl($C_{1-3}$)' for example, means methyl, ethyl, n-propyl or isopropyl, and 'alkyl($C_{1-4}$)' means methyl, ethyl, n-propyl, isopropyl, n-butyl, 2-butyl, isobutyl or 2-methyl-n-propyl.

The term 'acyl' means alkyl($C_{1-3}$) carbonyl, arylcarbonyl or aryl-alkyl($C_{1-3}$)carbonyl. 'Aryl' embraces monocyclic or fused bicyclic aromatic or hetero-aromatic groups, including but not limited to furyl, thienyl, pyrrolyl, oxazolyl, thiazolyl, imidazolyl, imidazo[2,1-b][1,3]thiazolyl, pyrazolyl, isoxazolyl, isothiazolyl, pyridyl, pyridazinyl, pyrimidinyl, pyrazinyl, 1,3,5-triazinyl, phenyl, indazolyl, indolyl, indolizinyl, isoindolyl, benzo[b]furanyl, 1,2,3,4-tetrahydro-naphtyl, 1,2,3,4-tetrahydroisoquinolinyl, indanyl, indenyl, benzo[b]thienyl, 2,3-dihydro-1,4-benzodioxin-5-yl, benzimidazolyl, benzothiazolyl, benzo[1,2,5]thia-diazolyl, purinyl, quinolinyl, isoquinolinyl, phtalazinyl, quinazolinyl, quinoxalinyl, 1,8-naphthyridinyl, naphthyl, pteridinyl or azulenyl. 'Halo' or 'Halogen' means chloro, fluoro, bromo or iodo; 'hetero' as in 'heteroalkyl, heteroaromatic' etc. means containing one or more N, O or S atoms. 'Heteroalkyl' includes alkyl groups with heteroatoms in any position, thus including N-bound O-bound or S-bound alkyl groups.

The term "substituted" means that the specified group or moiety bears one or more substituents. Where any group may carry multiple substituents, and a variety of possible substituents is provided, the substituents are independently selected, and need not to be the same. The term "unsubstituted" means that the specified group bears no substituents. With reference to substituents, the term "independently" means that when more than one of such substituents are possible, they may be the same or different from each other.

The terms "oxy", "thio" and "carbo" as used herein as part of another group respectively refer to an oxygen atom, a sulphur atom and a carbonyl (C=O) group, serving as a linker between two groups, such as for instance hydroxyl, oxyalkyl, thioalkyl, carboxyalkyl, etc. The term "amino" as used herein alone, or as part of another group, refers to a nitrogen atom that may be either terminal, or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine. The terms "sulfinyl" and "sulfonyl" as used herein as part of another group respectively refer to an —SO— or an —SO$_2$— group.

To provide a more concise description, the terms 'compound' or 'compounds' include tautomers, stereoisomers, N-oxides, isotopically-labelled analogues, or pharmacologically acceptable salts, hydrates or solvates, also when not explicitly mentioned.

As used herein, the term "leaving group" (L) shall mean a charged or uncharged atom or group that departs during a substitution or displacement reaction. The term refers to groups readily displaceable by a nucleophile, such as an amine, a thiol or an alcohol nucleophile. Such leaving groups are well known in the art. Examples include, but are not limited to, N-hydroxysuccinimide, N-hydroxybenzotriazole, halides (Br, Cl, I), triflates, mesylates, tosylates, and the like.

N-oxides of the compounds mentioned above belong to the invention. Tertiary amines may or may not give rise to N-oxide metabolites. The extent to what N-oxidation takes place varies from trace amounts to a near quantitative conversion. N-oxides may be more active than their corresponding tertiary amines, or less active. While N-oxides can easily be reduced to their corresponding tertiary amines by chemical means, in the human body this happens to varying degrees. Some N-oxides undergo nearly quantitative reductive conversion to the corresponding tertiary amines, in other cases conversion is a mere trace reaction, or even completely absent (Bickel, 1969).

Any compound metabolized in vivo to provide the bioactive agent (i.e., the compound of formula (1)) is a prodrug within the scope and spirit of the application. Prodrugs are therapeutic agents, inactive per se, but transformed into one or more active metabolites. Thus, in the methods of treatment of the present invention, the terms "administering" and "use in the treatment of" shall encompass treating the various disorders described with the compound specifically disclosed, or with a compound that not specifically disclosed, but that converts to the specified compound in vivo after administration to the patient. Prodrugs are bioreversible derivatives of drug molecules used to overcome some barriers to the utility of the parent drug molecule. These barriers include, but are not limited to, solubility, permeability, stability, presystemic metabolism and targeting limitations (Bundgaard, 1985; King, 1994; Stella, 2004; Ettmayer, 2004; Järvinen, 2005). Prodrugs, i.e., compounds that when administered to humans or mammals by any known route, are metabolised to compounds having formula (1), belong to the invention. In particular this relates to compounds with primary or secondary amino or hydroxy groups. Such compounds can be reacted with organic acids to yield compounds having formula (1) wherein an additional group is present that is easily removed after administration, for instance, but not limited to amidine, enamine, a Mannich base, a hydroxyl-methylene derivative, an O-(acyloxymethylene carbamate) derivative, carbamate, ester, amide or enaminone.

'Crystal form' refers to various solid forms of the same compound, for example polymorphs, solvates and amorphous forms. 'Polymorphs' are crystal structures in which a compound can crystallize in different crystal packing arrangements, all of which have the same elemental composition. Polymorphism is a frequently occurring phenomenon, affected by several crystallization conditions such as temperature, level of supersaturation, the presence of impurities, polarity of solvent, rate of cooling. Different polymorphs usually have different X-ray diffraction patterns, solid state NMR spectra, infrared or Raman spectra, melting points, density, hardness, crystal shape, optical and electrical properties, stability, and solubility. Recrystallization solvent, rate of crystallization, storage temperature, and other factors may cause one crystal form to dominate. 'Solvates' are generally a crystal form that contains either stoichiometric or non-stoichiometric amounts of a solvent. Often, during the process of crystallization some compounds have a tendency to trap a fixed molar ratio of solvent molecules in the crystalline solid state, thus forming a solvate. When the solvate is water, 'hydrates' may be formed. The compound of formula (1) and pharmaceutically acceptable salts thereof may exist in the form of a hydrate or a solvate, and such a hydrate and solvate are also encompassed in the present invention. Examples thereof include ¼ hydrate, dihydrochloride dihydrate, and the like. 'Amorphous' forms are noncrystalline materials with no long range order, and generally do not give a distinctive powder X-ray diffraction pattern. Crystal forms in general have been described by Byrn (1995) and Martin (1995)

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

Throughout the description and the claims of this specification the word "comprise" and variations of the word, such as "comprising" and "comprises" is not intended to exclude other additives, components, integers or steps.

While it may be possible for the compounds of formula (1) to be administered as the raw chemical, the compounds are typically presented as a 'pharmaceutical composition'. According to a further aspect, the present invention provides a pharmaceutical composition comprising at least one compound of formula (1), at least one pharmaceutically acceptable salt or solvate thereof, or a mixture of any of the foregoing, together with one or more pharmaceutically acceptable carriers thereof, and optionally one or more other therapeutic ingredients. The carrier(s) must be 'acceptable' in the sense of being compatible with the other ingredients of the formulation and not deleterious to the recipient thereof. The term "composition" as used herein encompasses a product comprising specified ingredients in predetermined amounts or proportions, as well as any product that results, directly or indirectly, from combining specified ingredients in specified amounts. In relation to pharmaceutical compositions, this term encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. The pharmaceutical composition includes enough of the active object compound to produce the desired effect upon the progress or condition of diseases. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The affinity of the compounds of the invention for $CB_1$ receptors and their inhibition of acetylcholinesterase, were determined as described below. From the binding affinity measured for a given compound of formula (1), one can estimate a theoretical lowest effective dose. At a concentration of the compound equal to twice the measured $K_i$-value, nearly 100% of the $CB_1$ receptors will be occupied by the compound. At a concentration of the compound equal to twice the measured inhibition constant, nearly 100% of the acetylcholinesterase will be occupied by the compound. By converting those concentrations to mg of compound per kg of patient one obtains a theoretical lowest effective dose, assuming ideal bioavailability. Pharmacokinetic, pharmacodynamic, and other considerations may alter the dose actually administered to a higher or lower value. The typical daily dose of the active ingredients varies within a wide range and will depend on various factors such as the relevant indication, the route of administration, the age, weight and sex of the patient, and may be determined by a physician. In general, total daily dose administration to a patient in single or individual doses, may be in amounts, for example, from 0.001 to 10 mg/kg body weight daily, and more usually from 0.01 to 1,000 mg per day, of total active ingredients. Such dosages will be administered to a patient in need of treatment from one to three times each day, or as often as needed for efficacy, and for periods of at least two months, more typically for at least six months, or chronically.

The term "therapeutically effective amount" as used herein refers to an amount of a therapeutic agent to treat a condition treatable by administrating a composition of the invention. That amount is the amount sufficient to exhibit a detectable therapeutic or ameliorative response in a tissue system, animal or human. The effect may include, for example, treating the conditions listed herein. The precise effective amount for a subject will depend upon the subject's size and health, the nature and extent of the condition being treated, recommendations of the treating physician (researcher, veterinarian, medical doctor or other clinician), and the therapeutics, or combination of therapeutics, selected for administration. Thus, it is not useful to specify an exact effective amount in advance. The term "pharmaceutically acceptable salt" refers to those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. They can be prepared in situ when finally isolating and purifying the compounds of the invention, or separately by reacting them with pharmaceutically acceptable non-toxic bases or acids, including inorganic or organic bases and inorganic or organic acids (Berge, 1977). The 'free base' form may be regenerated by contacting the salt with a base or acid, and isolating the parent compound in the conventional matter. The parent form of the compound differs from the various salt forms in certain physical properties, such as solubility in polar solvents, but otherwise the salts are equivalent to the parent form of the compound for the purposes of the present invention. 'Complex' refers to a complex of the compound of the invention, e.g., formula (1), complexed with a metal ion, where at least one metal atom is chelated or sequestered. Complexes are prepared by methods well known in the art (Dwyer, 1964).

The term "treatment" as used herein refers to any treatment of a mammalian, for example human condition or disease, and includes: (1) inhibiting the disease or condition, i.e., arresting its development, (2) relieving the disease or condition, i.e., causing the condition to regress, or (3) stopping the symptoms of the disease. The term 'inhibit' includes its generally accepted meaning which includes prohibiting, preventing, restraining, alleviating, ameliorating, and slowing, stopping or reversing progression, severity, or a resultant symptom. As such, the present method includes both medical therapeutic and/or prophylactic administration, as appropriate. As used herein, the term "medical therapy" intended to include prophylactic, diagnostic and therapeutic regimens carried out in vivo or ex vivo on humans or other mammals. 'Mammals' include animals of economic importance such as bovine, ovine, and porcine animals, especially those that produce meat, as well as domestic animals, sports animals, zoo animals, and humans. The term "subject" as used herein, refers to an animal, for example, a mammal such as a human, who has been the object of treatment, observation or experiment.

Abbreviations
AChE acetylcholinesterase
AD Alzheimer's disease
APT attached proton test
BOP benzotriazol-1-yl-oxytris-phosphonium hexafluorophosphate
$CB_1$ cannabinoid receptor subtype-1
$CB_2$ cannabinoid receptor subtype-2
CHO Chinese Hamster Ovary (cells)
CIP 2-chloro-1,3-dimethylimidazolinium hexafluorophosphate
DCC dicyclohexylcarbodiimide
DIPEA N,N-diisopropylethylamine
DMAP 4-dimethylaminopyridin
DMSO dimethylsulfoxide
HEK Human Embryonic Kidney (cells)
HBTU O-benzotriazol-1-yl-N,N,N',N'-tetramethyluronium hexafluorophosphate
HOAt N-hydroxy-7-azabenzotriazole
m.p. melting point c.q. melting range
MS mass spectrometry
PET positron emission tomography
p-TsOH paratoluene sulphonic acid
PyAOP 7-azabenzotriazol-1-yl-oxytris-(pyrrolidino)-phosphonium hexafluorophosphate
PyBOP benzotriazol-1-yl-oxytris(pyrrolidino)-phosphonium hexafluorophosphate
SPECT single photon emission computed tomography
TBTU O-(benzotriazol-1-yl)-N,N,N',N'-tetramethyluroniumtetrafluoroborate
THF tetrahydrofuran

EXAMPLE 1

Analytical Methods

Nuclear magnetic resonance spectra ($^1$H NMR and $^{13}$C NMR, APT) were determined in the indicated solvent using a Bruker ARX 400 ($^1$H: 400 MHz, $^{13}$C: 100 MHz) at 300 K, unless indicated otherwise. The spectra were determined in deuterated chloroform or dichloromethane obtained from Cambridge Isotope Laboratories Ltd. Chemical shifts (δ) are given in ppm downfield from tetramethylsilane ($^1$H, $^{13}$C) or $CCl_3F$ ($^{19}$F). Coupling constants J are given in Hz. Peak shapes in the NMR spectra are indicated with the symbols 'q' (quartet), 'dq' (double quartet), 't' (triplet), 'dt' (double triplet), 'd' (doublet), 'dd' (double doublet), 's' (singlet), 'bs' (broad singlet) and 'm' (multiplet).

Flash chromatography refers to purification using the indicated eluent and silica gel (either Acros: 0.030-0.075 mm or Merck silica gel 60: 0.040-0.063 mm). Column chromatography: Merck's silica gel 60 (0.063-0.200 mm) plates. Melting points were recorded on a Büchi B545 melting point apparatus. All reactions involving moisture sensitive compounds or conditions were carried out under an anhydrous nitrogen atmosphere. Reactions were monitored by using thin-layer chromatography (TLC) on silica coated plastic sheets (Merck precoated silica gel 60 F254) with the indicated eluent. Spots were visualised by UV light (254 nm) or 12. Dichloro-methane (phosphorous pentoxide and calciumhydride), tetrahydrofuran (sodium/benzophenone ketyl) and light petroleum (60-80) were distilled freshly prior to use. All other commercially available chemicals were used without further purification.

EXAMPLE 2

General Aspects of Syntheses

The syntheses of essential structural components of known cannabinoid-$CB_1$ antagonists are described in patent applications and/or scientific literature. For instance, well-documented are the essential cannabinoid structural components ($A^{1a}$) (WO01070700, Lange, 2004$^b$), ($A^{1b}$) (WO03026648), ($A^2$) (WO03027076, WO03040107, WO03063781, Lange, 2005[b]; Dyck (2004), (A[3]) (EP0576357, EP1150961, Lan, 1999; Seltzman, 1995; Dutta, 1994 and Katoch-Rouse, 2003), (A[4]) (WO03007887, Plummer, 2005), (A[5]) (WO0307069), (A[6]) (WO03078413, Lange, 2005[b]), (A[7]) (WO2004026301, Lange, 2005[b]; Dyck, 2004) and (A[8]) (WO2004013120).

In general terms, syntheses of compounds of formula (1) wherein n is 0, can be accomplished by reacting a compound of formula A-L, wherein L represents a leaving group, with a compound of formula B, wherein B is a nucleophile. Syntheses of compounds of formula (1) wherein n is 1, can be accomplished by reacting a compound of formula A-T-L, (L is a leaving group), with a compound of formula B wherein B is a nucleophile. Syntheses of compounds of formula (1) wherein n is 1 can also be accomplished by reacting a compound of formula A-L, (L is a leaving group) with a compound of formula T-B wherein T is a nucleophile. Another alternative is reacting a compound of formula A-T wherein T is a nucleophile, with a compound of general formula L-B, wherein L is a leaving group.

Specific syntheses of compounds of formula (1) wherein B is tacrine or a tacrine analog, is outlined in Scheme 2 below:

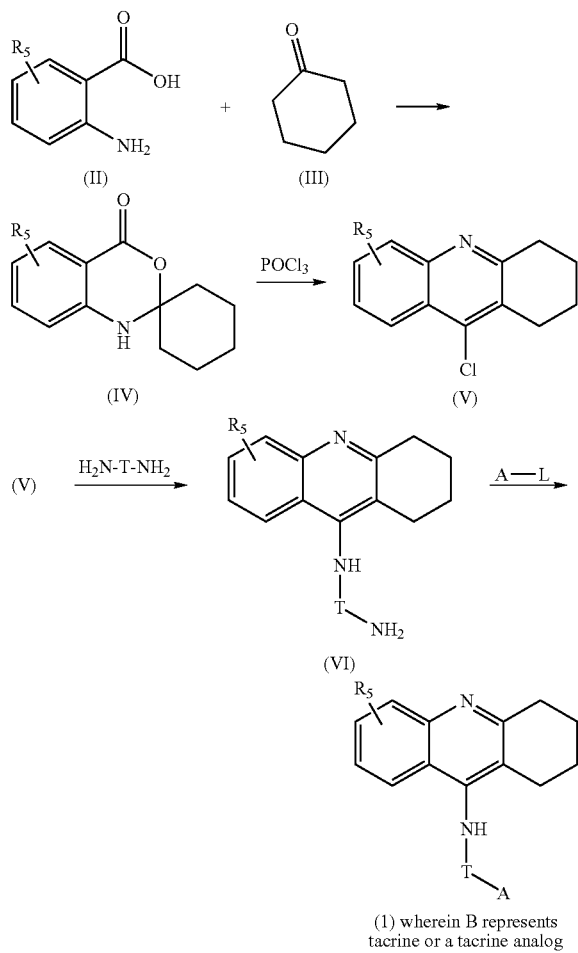

An anthranilic acid analog (II), wherein $R_5$ is chosen from a hydrogen or halogen atom, a methoxy group, a methyl group and a trifluoromethyl group, can be reacted with cyclohexanone (III) in an inert organic solvent such as toluene to give a spiro-compound of formula (IV). This compound of formula (IV) can be reacted with a chlorinating agent such as phosphorous oxychloride ($POCl_3$) to give a 9-chloro-1,2,3,4-tetrahydroacridine derivative (V) (Carlier, 1999[a]) that can be reacted with a compound of formula $H_2N$-T-$NH_2$ wherein the linker T is a saturated or unsaturated linear carbon chain having 2-8 carbon atoms, wherein the carbon chain may be substituted with 1-5 substituents chosen from a methyl group, an ethyl group, a hydroxy group, a fluoro atom, and an amino group, wherein the carbon chain optionally comprises an additional nitrogen atom, optionally substituted with an $C_{1-3}$ alkyl group, or wherein the carbon chain optionally comprises an additional oxygen, sulphur atom, carbonyl group, sulfonyl group, amide (C(=O)—NH) group, sulfonamide (S($O_2$)—NH) group, ureido group, phenyl group, or aryl group, wherein each phenyl group or aryl group is optionally substituted with 1-4 substituents chosen from a halogen atom, a cyano group, a methyl group, a methoxy group, a trifluoromethyl group, $OCHF_2$, $OCF_3$, $SCF_3$, and a nitro group, to give a compound of general formula (VI). This reaction is usually carried out in an inert organic solvent such as 1-pentanol at an elevated temperature (Carlier, 1999[b]). A compound of formula (VI) can be reacted with a compound of formula A-L, wherein A is an essential structural component of any known cannabinoid-$CB_1$ antagonist comprising at least two phenyl rings, wherein each phenyl is optionally substituted with one or two substituents chosen from a halogen atom, a methoxy group, and a trifluoromethyl group, said essential structural component being connected to a hydrogen bond acceptor in said cannabinoid-$CB_1$ antagonist, wherein the hydrogen bond acceptor moiety is chosen from a carbonyl group, a sulfonyl group, and a nitrogen or oxygen atom incorporated in a heteroaromatic ring structure, and L is a leaving group. When L is a hydroxy group which is part of a carboxylic acid group, activating or coupling reagents may be added in order to enhance the reaction rate (Bodanszky, 1994; Akaji, 1994; Albericio, 1997). This reaction can give a compound of formula (1) wherein A has the meaning as given above, T is a linker with the above-mentioned meaning, and B is tacrine or a tacrine analog.

Syntheses of compounds of formula (1) wherein A is one of ($A^{1a}$) or ($A^{1b}$), wherein each of $R^1$, $R^2$ and $R^3$ is chosen from a hydrogen atom, a trifluoromethyl group, and a halogen atom, is outlined in Scheme 3 below:

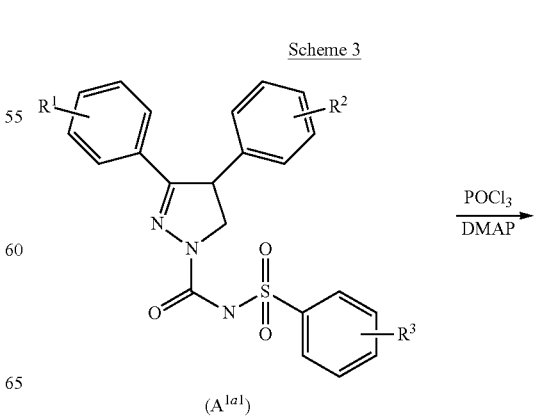

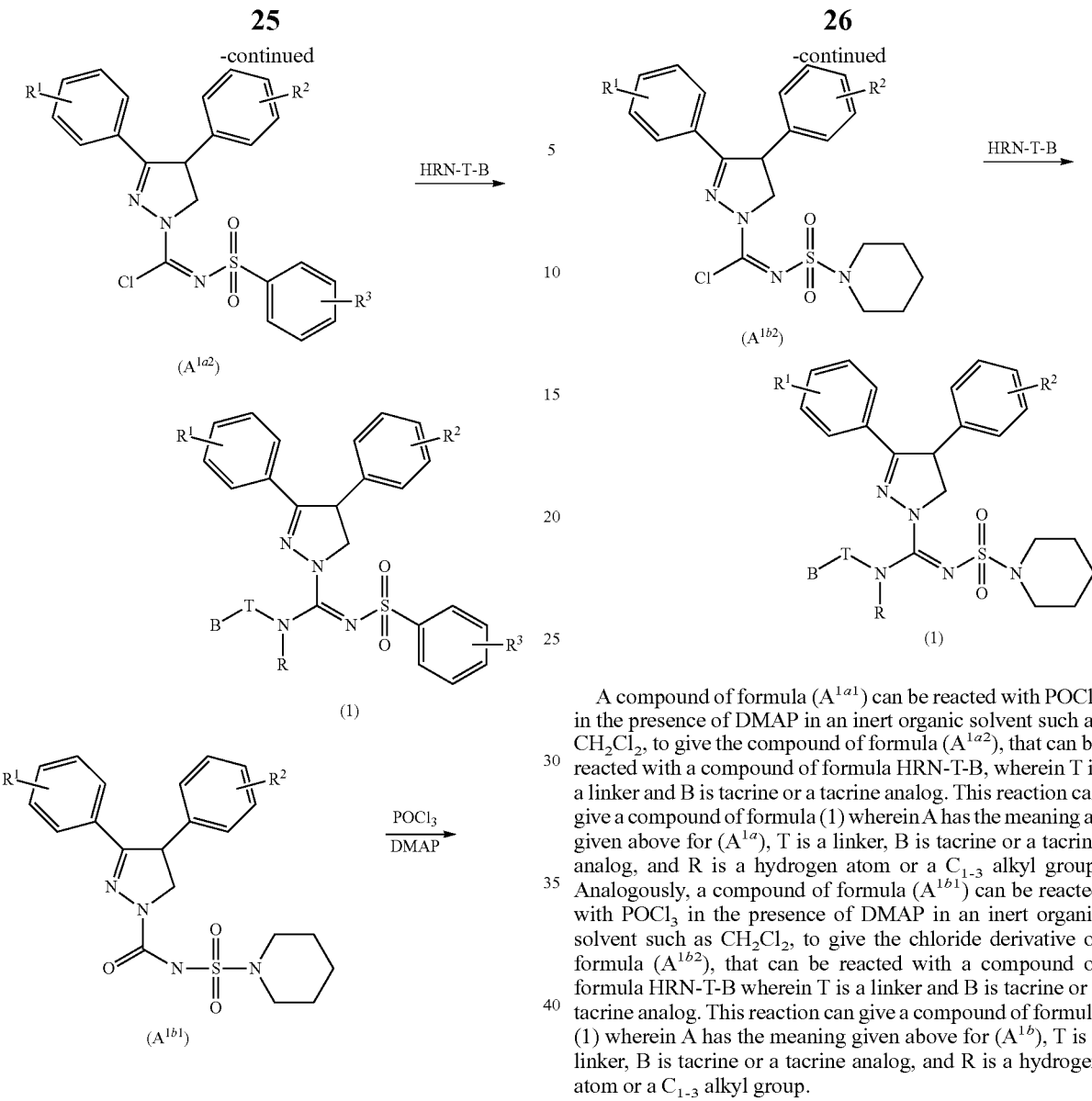

A compound of formula ($A^{1a1}$) can be reacted with $POCl_3$ in the presence of DMAP in an inert organic solvent such as $CH_2Cl_2$, to give the compound of formula ($A^{1a2}$), that can be reacted with a compound of formula HRN-T-B, wherein T is a linker and B is tacrine or a tacrine analog. This reaction can give a compound of formula (1) wherein A has the meaning as given above for ($A^{1a}$), T is a linker, B is tacrine or a tacrine analog, and R is a hydrogen atom or a $C_{1-3}$ alkyl group. Analogously, a compound of formula ($A^{1b1}$) can be reacted with $POCl_3$ in the presence of DMAP in an inert organic solvent such as $CH_2Cl_2$, to give the chloride derivative of formula ($A^{1b2}$), that can be reacted with a compound of formula HRN-T-B wherein T is a linker and B is tacrine or a tacrine analog. This reaction can give a compound of formula (1) wherein A has the meaning given above for ($A^{1b}$), T is a linker, B is tacrine or a tacrine analog, and R is a hydrogen atom or a $C_{1-3}$ alkyl group.

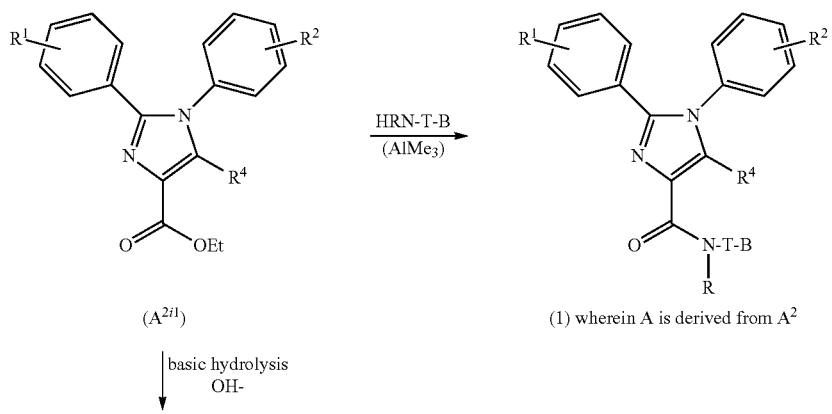

Scheme 4

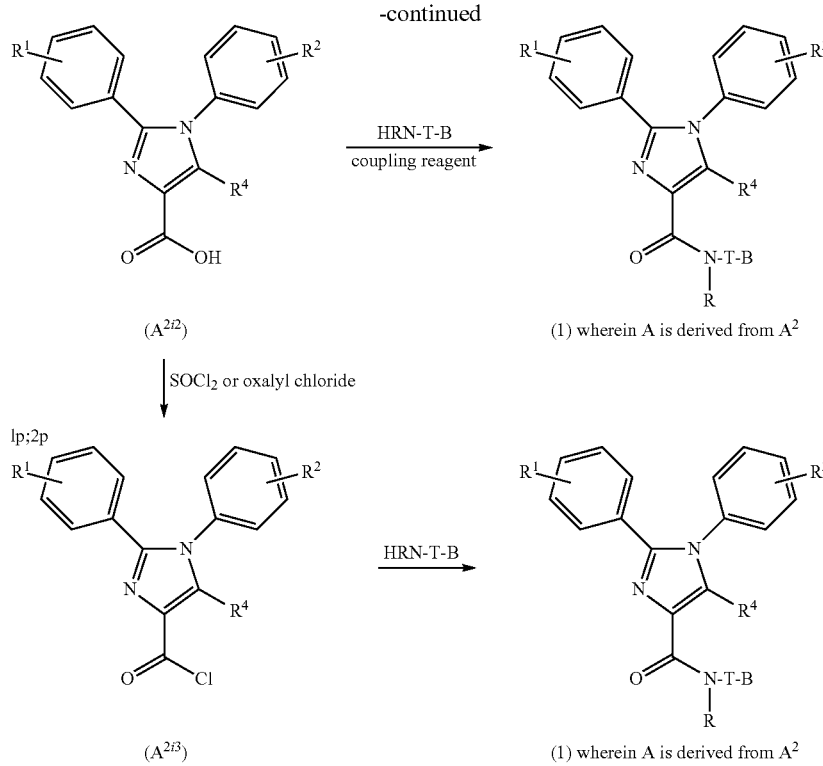

Syntheses of compounds of formula (1) wherein A is (A²) is outlined in Scheme 4 above, wherein R is a hydrogen atom or a $C_{1-3}$ alkyl group, each of $R^1$ and $R^2$ is chosen from a hydrogen atom, a trifluoromethyl group, and a halogen atom, $R_4$ is chosen from a hydrogen or halogen atom, a methyl group, an ethyl group, a trifluoromethyl group, a hydroxymethyl group, a fluoromethyl group, a 2,2,2-trifluoroethyl group, a propyl group, a methylsulfanyl group, a methylsulfinyl group, a methylsulfonyl group, an ethylsulfanyl group, an ethylsulfinyl group, an ethylsulfonyl group, a $C_{1-3}$-dialkylaminomethyl group, a pyrrolidin-1-ylmethyl group, a piperidin-1-ylmethyl group, and a morpholin-4-ylmethyl group, and the other symbols have the meanings as given above. An ester of formula ($A^{2i1}$) can be reacted with a compound of formula HRN-T-B to give a compound A-T-B of formula (1) wherein part A is derived from substructure $A^2$. Such a reaction can be catalyzed by trimethylaluminum $AlMe_3$ (Levin, 1982).

Alternatively, a compound of formula ($A^{2i1}$) can be hydrolyzed to the corresponding carboxylic acid of formula ($A^{2i2}$). A compound of formula ($A^{2i2}$) can be reacted with a compound of formula HRN-T-B to give a compound of formula (1) wherein part A is derived from substructure $A^2$. It is possible that this reaction proceeds via activating and coupling methods such as formation of an active ester, or in the presence of a so-called coupling reagent, for example, DCC, HBTU, TBTU, HOAt, PyBOP, BOP, CIP, 2-chloro-1,3-dimethylimidazolinium chloride or PyAOP (Bodanszky, 1994; Akaji, 1994; Albericio, 1997; Montalbetti, 2005). Alternatively, a compound of formula ($A^{2i2}$) can be converted in the presence of a chlorinating agent such as thionyl chloride or oxalyl chloride, to the corresponding acid chloride of formula ($A^{2i3}$). A compound of formula ($A^{2i3}$) can be reacted with a compound of formula HRN-T-B to give a compound of formula (1) wherein part A is derived from substructure $A^2$. A base like DIPEA can be added to the reaction mixture to scavenge the liberated hydrochloric acid, or excess HRN-T-B can be applied for this purpose.

Analogously, the substructures of ($A^3$) ($A^4$), ($A^5$), ($A^6$), ($A^7$), or ($A^8$), as shown above, can be converted into compounds A-T-B of the formula (1) wherein part A is derived from the substructures ($A^3$) ($A^4$), ($A^5$), ($A^6$), ($A^7$), or ($A^8$), respectively.

The selection of the particular synthetic procedures depends on factors known to those skilled in the art such as the compatibility of functional groups with the reagents used, the possibility to use protecting groups, catalysts, activating and coupling reagents and the ultimate structural features present in the final compound being prepared.

Pharmaceutically acceptable salts may be obtained using standard procedures well known in the art, for example by mixing a compound of the present invention with a suitable acid, for instance an inorganic acid or an organic acid.

EXAMPLE 3

Syntheses of Specific Compounds

The specific compounds of which the synthesis is described below are intended to further illustrate the invention in more detail, and therefore do not restrict the scope of the invention in any way. Other embodiments of the invention will be apparent to those skilled in the art from consideration of the specification and practice of the invention disclosed herein. It is thus intended that the specification and examples be considered as exemplary only.

Compound 1

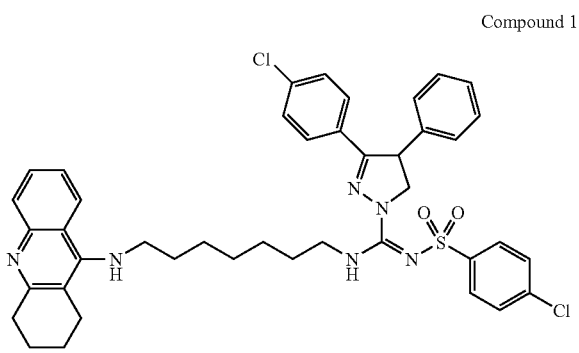

Compound 2

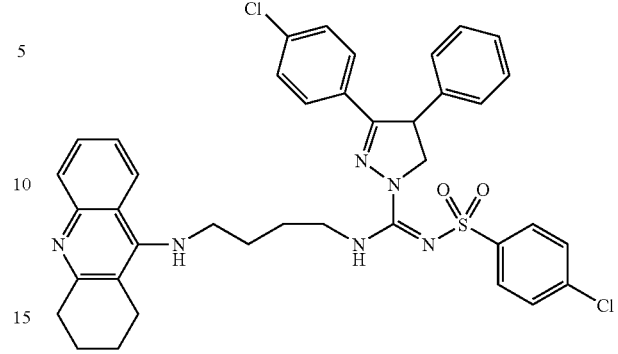

Part A: Spiro[2H-3,1-benzoxazine-2,1'-cyclohexan-4(1H)]-one was synthesized from antranilic acid and cyclohexanone, in toluene, in 73% yield, as described (Carlier, 1999[a]). The compound was converted to 9-chloro-1,2,3,4-tetrahydroacridine (Carlier, 1999[a]) in 99% yield, and reacted with 1,2-diaminoheptane in 1-pentanol, giving N-[9'-(1',2',3',4'-tetrahydro-acridinyl)]-1,7-diaminoheptane (Carlier, 1999[b]).

Analogously, N-[9'-(1',2',3',4'-tetrahydroacridinyl)]-1,7-diaminobutane was prepared from 1,2-diaminobutane and 9-chloro-1,2,3,4-tetrahydroacridine in 78% yield. N-[9'-(1',2',3',4'-tetrahydroacridinyl)]-1,7-diaminobutane: $^1$H-NMR (400 MHz, CDCl$_3$): δ 1.53-1.61 (m, 2H), 1.69-1.77 (m, 2H), 1.91-2.20 (m, 6H), 2.70-2.78 (m, 4H), 3.08 (br s, 2H), 3.45-3.55 (m, 2H), 4.31 (br s, 1H), 7.27-7.37 (m, 1H), 7.53-7.58 (m, 1H), 7.93-7.99 (m, 2H).

Part B: 3-(4-Chlorophenyl)-N-[(4-chlorophenyl)sulfonyl]-4-phenyl-4,5-dihydro-1H-pyrazole-1-carboxamide was obtained as described (Lange, 2004[b]). This compound (1.5 gram, 3.16 mol) was dissolved in dichloromethane (30 ml) and DMAP (1.707 gram, 13.9 mmol) and POCl$_3$ (0.59 g, 3.85 mmol) were successively added and the resulting mixture was refluxed for 5 hours. The mixture was allowed to attain room temperature and was concentrated in vacuo to give crude 3-(4-chlorophenyl)-N-[(4-chlorophenyl)sulfonyl]-4-phenyl-4,5-dihydro-1H-pyrazole-1-carboximidoyl chloride. The obtained 3-(4-chlorophenyl)-N-[(4-chlorophenyl)sulfonyl]-4-phenyl-4,5-dihydro-1H-pyrazole-1-carboximidoyl chloride was dissolved in dichloromethane (30 ml) and reacted at 0° C. with N-[9'-(1',2',3',4'-tetrahydro-acridinyl)]-1,7-diaminoheptane (1.48 gram, 4.75 mmol) and DIPEA (1.02 gram, 7.9 mmol) at reflux temperature for 72 hours. The mixture was allowed to attain room temperature and was washed with water and brine successively, dried over Na$_2$SO$_4$, filtered and concentrated. The obtained crude product was purified by flash chromatography (gradient: dichloromethane=>dichloromethane/methanol=95/5 (v/v)) to give pure 4-chloro-N-{[3-(4-chlorophenyl)-4-phenyl-4,5-dihydro-1H-pyrazolyl]-[7-(1,2,3,4-tetrahydroacridin-9-ylamino)-heptylamino]methylene}benzene-sulfonamide (compound 1) (0.85 gram, 35% yield). Melting point: 87-89° C.

Analogously 4-chloro-N-{[3-(4-chlorophenyl)-4-phenyl-4,5-dihydro-1H-pyrazolyl]-[7-(1,2,3,4-tetrahydroacridin-9-yl-amino)butylamino]methylene}benzene sulfonamide (compound 2, m.p.: 87-89° C.). was prepared from 3-(4-chlorophenyl)-N-[(4-chloro-phenyl)sulfonyl]-4-phenyl-4,5-dihydro-1H-pyrazole-1-carboxamide and N-[9'-(1',2',3',4'-tetrahydro-acridinyl)]-1,7-diamino-butane.

Compound 3
Part A: Ethyl 2-(2-chlorophenyl)-1-(4-chlorophenyl)-5-ethyl-1H-imidazole-4-carboxylate was obtained according to WO03040107. To a magnetically stirred solution of ethyl 2-(2-chlorophenyl)-1-(4-chlorophenyl)-5-ethyl-1H-imidazole-4-carboxylate (5.80 g, 0.0149 mol) in tetrahydrofuran (40 ml) was added a solution of LiOH (0.715 g) in water (40 ml). The resulting mixture was heated at 70° C. for 16 hours. The resulting mixture was allowed to attain room temperature and subsequently treated with concentrated hydrochloric acid (3.5 ml). The tetrahydrofuran was evaporated in vacuo and the resulting mixture was stirred overnight. The formed precipitate was collected by filtration and washed with petrolaum ether (40-60) to give 2-(2-chlorophenyl)-1-(4-chlorophenyl)-5-ethyl-1H-imidazole-4-carboxylic acid (4.52 gram, 84% yield). $^1$H-NMR (400 MHz, CDCl$_3$): δ 1.09 (t, J=7, 3H), 2.90 (q, J=7, 2H), 3.70 (br s, 1H), 7.12 (dt, J=8 and 2, 2H), 7.22-7.28 (m, 1H), 7.29-7.38 (m, 5H).

Part B: To a magnetically stirred solution of N-[9'-(1',2',3',4'-tetrahydro-acridinyl)]-1,7-diaminoheptane (3.25 g, 10.4 mmol) in dichloromethane (50 ml) was successively added 2-(2-chlorophenyl)-1-(4-chlorophenyl)-5-ethyl-1H-imidazole-4-carboxylic acid (2.8 gram, 7.8 mmol), HOAt (1.3 gram, 9.4 mmol) and 1-(3-dimethylaminopropyl)-3-ethylcarbodiimide hydrochloride (1.8 gram, 9.4 mmol). The resulting mixture was stirred at room temperature for 60 hours and successively washed with water (2×100 ml) and brine (100 ml). The organic layer was successively dried over Na$_2$SO$_4$, filtered and concentrated. The obtained crude product was purified by flash chromatography (gradient:dichloromethane/ethanol=99/1=>dichloromethane/methanol=90/10 (v/v)) to give pure N-[7-(1,2,3,4-tetrahydroacridin-9-ylamino)heptyl]-2-(2-chlorophenyl)-1-(4-chlorophenyl)-5-ethyl-1H-imidazole-4-carboxamide (compound 3) (2.25 g, 53% yield). Melting point: 143-145° C.

compound 3

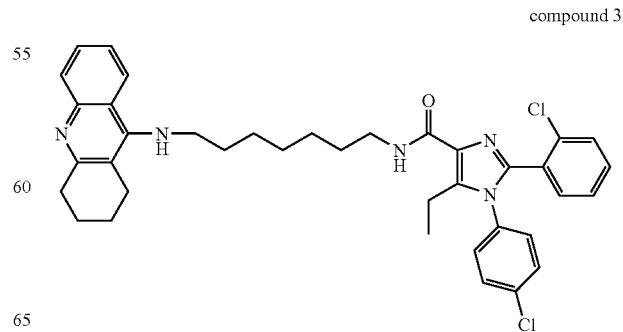

Analogously N-[4-(1,2,3,4-tetrahydroacridin-9-ylamino)butyl]-2-(2-chlorophenyl)-1-(4-chlorophenyl)-5-ethyl-1H-imidazole-4-carboxamide (compound 4, m.p.: 103-105° C.) was prepared from 2-(2-chlorophenyl)-1-(4-chlorophenyl)-5-ethyl-1H-imidazole-4-carboxylic acid and N-[9'-(1',2',3',4'-tetrahydroacridinyl)]-1,7-diaminobutane.

compound 4

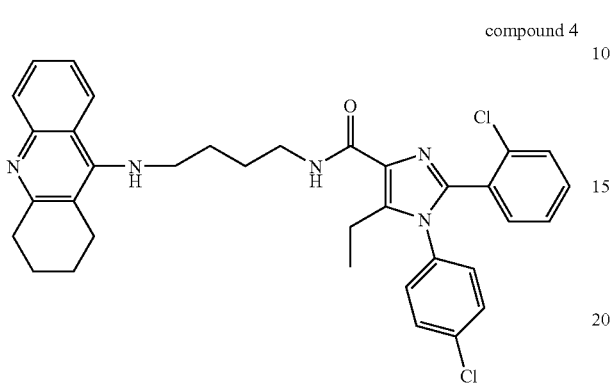

EXAMPLE 4

Formulations

For oral (p.o.) administration: to the desired quantity (0.5-5 mg) of compound 1 in a glass tube, some glass beads were added and the solid was milled by vortexing for 2 min. After addition of 1 ml of a solution of 1% methylcellulose in water and 2% (v/v) Poloxamer 188 (Lutrol F68), the compound was suspended by vortexing for 10 min. The pH was adjusted to 7 with a few drops of aqueous NaOH (0.1N). Remaining particles in the suspension were further suspended by using an ultrasonic bath.

For intraperitoneal (i.p.) administration: to the desired quantity (0.5-15 mg) of the solid compound 1 in a glass tube, some glass beads were added and the solid was milled by vortexing for 2 minutes. After addition of 1 ml of a solution of 1% methylcellulose and 5% mannitol in water, the compound was suspended by vortexing for 10 minutes. Finally the pH was adjusted to 7.

EXAMPLE 5

Pharmacological Methods

In vitro affinity for human cannabinoid-$CB_1$ receptors was determined using membrane preparations of CHO cells in which the human cannabinoid $CB_1$ receptor is stably transfected, and [$^3$H]CP-55,940 as radioligand. After incubation of a freshly prepared cell membrane preparation with the [$^3$H]-ligand, with or without addition of compounds of the invention, separation of bound and free ligand was performed by filtration over glass fiber filters. Radioactivity on the filter was measured by liquid scintillation counting.

Inhibition of acetylcholinesterase in human HEK-293 cells.

Compounds were dissolved in DMSO (10 mM) and diluted to test concentrations in assay buffer. Testing was at a 3 log concentration range around a predetermined $IC_{50}$ for the respective assay: e.g., 10, 1, 0.1 and 0.01 PM for $IC_{50}$ of 0.3 μM and 300, 30, 3, and 0.3 nM for one with $IC_{50}$ of 10 nM. All determinations were performed as duplicates. The highest concentration tested for primes was 10 PM. Following incubation of the test compound with an acetylcholinesterase enzyme preparation (human recombinant expressed in HEK-293 cells) and the substrate acetylthiocholine (50 μM) for 30 minutes at 37° C., the thio-conjugate product was determined by photometry. Results were expressed as % of total product formed, at each concentration tested (duplicates); from the concentration—production inhibition curves $IC_{50}$ values were determined by non-linear regression analysis using Hill equation curve fitting. Results were expressed as $pIC_{50}$'s. Compounds with no significant affinity at concentrations of 10 μM and higher were considered inactive: $pIC_{50}$<5.0. (Ellman, 1961).

EXAMPLE 6

Pharmacological Test Results $CB_1$ receptor affinity data and acetylcholinesterase inhibition data obtained according to the protocols given above are shown in the table below.

| | In vitro pharmacology | |
|---|---|---|
| | Cannabinoid-$CB_1$ receptor binding $pK_i$ | Acetylcholinesterase inhibition $pIC_{50}$ |
| Present invention | | |
| compound 1 | 7.3 | 6.0 ± 0.3 |
| compound 2 | 7.4 | 5.6 ± 0.4 |
| compound 3 | 7.2 | 5.9 ± 0.3 |
| compound 4 | 7.5 | 6.5 ± 0.3 |
| $CB_1$ antagonists | | |
| rimonabant | 7.2 | 4.6 ± 0.2 |
| SLV319 | 8.1 | 5.2 ± 0.1 |
| WO 03/027076* | 7.9 | <4.5 |
| cholinesterase inhibitors | | |
| tacrine | <6.0 | 6.6 |

The results clearly indicate that the compounds of the invention have affinity for cannabinoid-$CB_1$ receptors and cholinesterase inhibiting activity. Their affinity is as potent as that of rimonabant, while e.g., compound 4, simultaneously is as potent a cholinesterase inhibitor as tacrine. This in sharp contrast with for instance a structurally closely related potent $CB_1$ antagonist disclosed in WO 03/027076 (see structures below) which is completely inactive as a cholinesterase inhibitor.

WO 03/027076

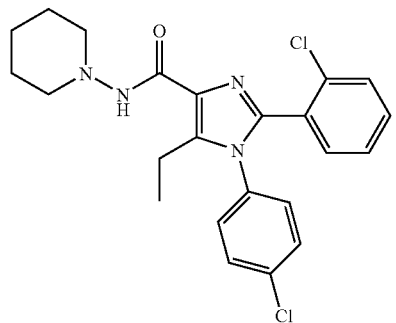

-continued compound 4

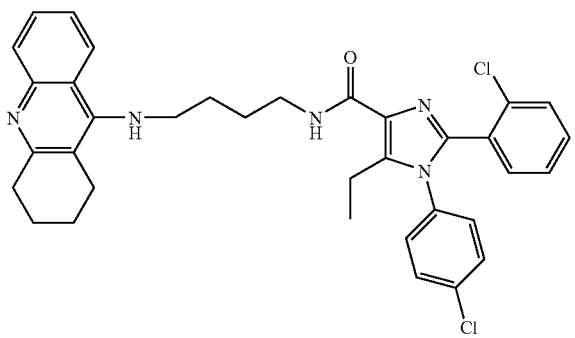

EXAMPLE 7

Pharmaceutical Preparations

For clinical use, compounds of formula (1) are formulated into pharmaceutical compositions that are important and novel embodiments of the invention because they contain the compounds, more particularly specific compounds disclosed herein. Types of pharmaceutical compositions that may be used include, but are not limited to, tablets, chewable tablets, capsules (including microcapsules), solutions, parenteral solutions, ointments (creams and gels), suppositories, suspensions, and other types disclosed herein, or are apparent to a person skilled in the art from the specification and general knowledge in the art. The active ingredient for instance, may also be in the form of an inclusion complex in cyclodextrins, their ethers or their esters. The compositions are used for oral, intravenous, subcutaneous, tracheal, bronchial, intranasal, pulmonary, transdermal, buccal, rectal, parenteral or other ways to administer. The pharmaceutical formulation contains at least one compound of formula (1) in admixture with at least one pharmaceutically acceptable adjuvant, diluent and/or carrier. The total amount of active ingredients suitably is in the range of from about 0.1% (w/w) to about 95% (w/w) of the formulation, for example from 0.5% to 50% (w/w), or from 1% to 25% (w/w). In some embodiments, the amount of active ingredient is greater than about 95% (w/w) or less than about 0.1% (w/w).

The compounds of the invention can be brought into forms suitable for administration by means of usual processes using auxiliary substances such as liquid or solid, powdered ingredients, such as the pharmaceutically customary liquid or solid fillers and extenders, solvents, emulsifiers, lubricants, flavorings, colorings and/or buffer substances. Frequently used auxiliary substances include magnesium carbonate, titanium dioxide, lactose, saccharose, sorbitol, mannitol and other sugars or sugar alcohols, talc, lactoprotein, gelatin, starch, amylopectin, cellulose and its derivatives, animal and vegetable oils such as fish liver oil, sunflower, groundnut or sesame oil, polyethylene glycol and solvents such as, for example, sterile water and mono- or polyhydric alcohols such as glycerol, as well as with disintegrating agents and lubricating agents such as magnesium stearate, calcium stearate, sodium stearyl fumarate and polyethylene glycol waxes. The mixture may then be processed into granules or pressed into tablets. A tablet can be prepared using the ingredients below:

| Ingredient | Quantity (mg/tablet) |
| --- | --- |
| COMPOUND No. 1 | 10 |
| Cellulose, microcrystalline | 200 |
| Silicon dioxide, fumed | 10 |
| Stearic acid | 10 |
| Total | 230 |

The components are blended and compressed to form tablets each weighing 230 mg.

The active ingredients may be separately premixed with the other non-active ingredients, before being mixed to form a formulation. The active ingredients may also be mixed with each other, before being mixed with the non-active ingredients to form a formulation.

Soft gelatin capsules may be prepared with capsules containing a mixture of the active ingredients of the invention, vegetable oil, fat, or other suitable vehicle for soft gelatin capsules. Hard gelatin capsules may contain granules of the active ingredients. Hard gelatin capsules may also contain the active ingredients together with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories that contain the active substance mixed with a neutral fat base; (ii) in the form of a gelatin rectal capsule that contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations may be prepared in the form of syrups, elixirs, concentrated drops or suspensions, e.g., solutions or suspensions containing the active ingredients and the remainder consisting, for example, of sugar or sugar alcohols and a mixture of ethanol, water, glycerol, propylene glycol and polyethylene glycol. If desired, such liquid preparations may contain coloring agents, flavoring agents, preservatives, saccharine and carboxymethyl cellulose or other thickening agents. Liquid preparations may also be prepared in the form of a dry powder, reconstituted with a suitable solvent prior to use. Solutions for parenteral administration may be prepared as a solution of a formulation of the invention in a pharmaceutically acceptable solvent. These solutions may also contain stabilizing ingredients, preservatives and/or buffering ingredients. Solutions for parenteral administration may also be prepared as a dry preparation, reconstituted with a suitable solvent before use.

Also provided according to the invention are formulations and 'kits of parts' comprising one or more containers filled with one or more of the ingredients of a pharmaceutical composition of the invention, for use in medical therapy. Associated with such container(s) can be written materials such as instructions for use, or a notice in the form prescribed by a governmental agency regulating the manufacture, use or sale of pharmaceuticals products, which notice reflects approval by the agency of manufacture, use, or sale for human or veterinary administration. The use of formulations of the invention in the manufacture of medicaments for treating a condition wherein antagonism of $CB_1$ receptors and/or inhibition of acetylcholinesterase is required or desired, and methods of medical treatment or comprising the administration of a therapeutically effective total amount of at least one compound of formula (1), either as such or, in the case of prodrugs, after administration, to a patient suffering from, or susceptible to, a condition wherein antagonism of $CB_1$ receptors and/or inhibition of acetylcholinesterase is required or desired.

By way of example and not of limitation, several pharmaceutical compositions are given, comprising examples of active compounds for systemic use or topical application are described herein. Other compounds of the invention or combinations thereof, may be used in place of (or in addition to) said compounds. The concentration of the active ingredient may be varied over a wide range as discussed herein. The amounts and types of ingredients that may be included are well known in the art.

BIBLIOGRAPHY

Akaji, K. et al., Tetrahedron Lett. (1994), 35, 3315-3318.
Albericio, F. et al., Tetrahedron Lett. (1997), 38, 4853-4856.
Berge, S. M.: "Pharmaceutical salts", J. Pharmaceutical Science, 66, 1-19 (1977).
Berger, C. et al., J. Neurochem. 2004, 88, 1159-1167.
Bickel, M. H.: "The pharmacology and Biochemistry of N-oxides", Pharmacological Reviews, 21(4), 325-355, 1969.
Bodanszky, M. and A. Bodanszky: The Practice of Peptide Synthesis, Springer-Verlag, New York, 1994; ISBN: 0-387-57505-7.
Brufani M. et al., Drugs of the Future 1997, 22, 397-410.
Bundgaard, H. (editor), "Design of Prodrugs", Elsevier, 1985.
Byrn et al., Pharmaceutical Research, 12(7), 945-954, 1995.
Carlier, P. R. et al., Bioorg. Med. Chem. 1999[a], 7, 351-357.
Carlier, P. R. et al., J. Med. Chem. 1999[b], 42, 4225-4231.
Castellano, C. et al., Curr. Drug Targets, CNS Neurol. Disorders, 2003, 2, 389-402.
Cohen, C. et al., Behav. Pharmacol. 2002, 13, 451-463.
Darvesh, S. et al., Nature Rev. Neurosci. 2003, 4, 131-138.
De Groot, A. et al., Mol. Pharmacol. 2006, 70, 1236-1245.
De Petrocellis, L. et al., Br. J. Pharmacol. 2004, 141, 765-774.
Di Marzo, V. et al., Nature Rev. Drug Discov. 2004, 3, 771-784.
Dutta, A. K. et al., Med. Chem. Res. 1994, 5, 54-62.
Dwyer & Meilor: "Chelating agents and Metal Chelates", Academic Press, chapter 7, 1964.
Dyck, B. et al., Bioorg. Med. Chem. Lett. 2004, 14, 1151-1154.
Ellman, G. L., Courtney, K. D., Andres, V. and Featherstone, R. M. (1961) A new and rapid calorimetric determination of acetylcholinesterase activity. Biochem. Pharmacol., 7: 88-95.
Ettmayer, P. et al., "Lessons learned from marketed and investigational prodrugs", J. Med. Chem., 47, 2393-2404, 2004.
Hertzog, D. L. Expert Opin. Ther. Patents 2004, 14, 1435-1452.
Hikida, T. et al., PNAS, 2003, 100, 6169-6173.
Hungund, B. L. et al., Alcohol Clin. Exp. Res. 2002, 26, 565-574.
Järvinen, T. et al., "Design and Pharmaceutical applications of prodrugs", pages 733-796 in: S. C. Gad (editor): "Drug Discovery HandbooK", John Wiley & Sons Inc., New Jersey, U.S.A., 2005.
Katoch-Rouse, R. et al., J. Med. Chem. 2003, 46, 642-645.
King, F. D., (editor), page 215 in: "Medicinal Chemistry: Principles and Practice", 1994, ISBN 0-85186-494-5.
Kumar, V. et al., Eur J Neurol 7 (2000), pp. 159-169.
Lambert, D. M. and Fowler, C. J. J. Med. Chem. 2005, 48, 5059-5087.
Lan, R. et al., J. Med. Chem. 1999, 42, 769-776.
Landsman, R. S. et al., Eur. J. Pharmacol. 1997, 334, R1-R2.
Lange, J. H. M. and Kruse, C. G., C. Curr. Opin. Drug Discovery Dev. 2004, 7, 498-506.
Lange, J. H. M. et al., J. Med. Chem. 2004[b], 47, 627-643.
Lange, J. H. M. and Kruse, C. G. Drug Discov. Today 2005, 10, 693-702.
Lange, J. H. M. et al., J. Med. Chem. 2005[b], 48, 1823-1838.
Levin, J. I., E. Turos and S. M. Weinreb, Synth. Commun., 12, 989-993, 1982.
Lichtman, A. H. et al., Prostaglandins Leukotrienes and Essential Fatty Acids 2002, 66, 269-285.
Marco, J. L. and Carreras, M. C., Mini-Rev. Med. Chem. 2003, 3, 518-514.
Martin, E. W. (Editor), "Remington: The Science and Practice of Pharmacy", Mack Publishing Company, 19th Edition, Easton, Pa., Vol 2., Chapter 83, 1447-1462, 1995.
Masanic, C. A. et al., Arch Phys Med Rehabil 82 (2001), 896-901.
McKeith, I. et al., Lancet 356 (2000), 2031-2036.
Montalbetti, C. and V. Falque, Tetrahedron, 61, 10827-10852, 2005.
Muccioli, G. G. et al., Curr. Med. Chem. 2005, 12, 1361-1394.
Padgett, L. W. Life Sciences 2005, 77, 1767-1798.
Plummer, C. W. et al., Bioorg. Med. Chem. Lett. 2005, 15, 1441-1446.
Racchi, M. et al., Pharmacol Res. 2004, 50, 441-451).
Reggio, P. H., Curr. Pharm. Des. 2003, 9, 1607-1633.
Seltzman, H. H. et al., J. Chem. Soc. Chem. Commun. 1995, 1549-1550.
Smith, R. A. and Fathi, Z. IDrugs 2005, 8, 53-66.
Solinas, M. et al., J. Pharmacol. Exp. Ther. 2003, 306, 93-102.
Spencer, C. M. and Noble, S. Drugs Aging 13 (1998), 391-411.
Stella, J., "Prodrugs as therapeutics", Expert Opin. Ther. Patents, 14(3), 277-280, 2004.
Terry, A. V. and Buccafusco, J. J., J. Pharmacol. Exp. Ther. 2003, 306, 821-827.
Thakur, G. A. et al., Mini-Rev. Med. Chem. 2005, 5, 631-640.
Vandevoorde, S. & Lambert, D. M. Curr. Pharm. Des. 2005, 11, 2647-68.
Weinstock, M. CNS Drugs 1999, 12, 307.
Werber, E. A. and Rabey, J. M., J Neural Transm 108 (2001), 1319-1325).
Wolff, M. C. and Leander, J. D., Eur. J. Pharmacol. 2003, 477, 213-217.

What is claimed is:

1. A compound of formula (1):

$$A-(T)_n-B \quad (1)$$

or a tautomer, stereoisomer, N-oxide, or a pharmacologically acceptable salt of any of the foregoing, wherein:

A is chosen from one of:

wherein X is a sulfonyl or a carbonyl group, the sign + is the position at which one of (A$^{1a}$) to (A$^8$) is connected to T of formula (1), each of R$^1$, R$^2$ and R$^3$ is chosen from a hydrogen atom, a trifluoromethyl group, and a halogen atom, R$_4$ is chosen from a hydrogen atom, a halogen atom, a methyl group, an ethyl group, a trifluoromethyl group, a hydroxymethyl group, a fluoromethyl group, a 2,2,2-trifluoroethyl group, a propyl group, a methylsulfanyl group, a methylsulfinyl group, a methylsulfonyl group, an ethylsulfanyl group, an ethylsulfinyl group, an ethylsulfonyl group, a C$_{1-3}$-dialkylaminomethyl group, a pyrrolidin-1-ylmethyl group, a piperidin-1-ylmethyl group, and a morpholin-4-ylmethyl group, and R is a hydrogen atom or a C$_{1-3}$ alkyl group;

T is chosen from a saturated or unsaturated linear carbon chain having from 2 to 8 carbon atoms, wherein the carbon chain is optionally substituted with from 1 to 5 substituents chosen from a methyl group, an ethyl group, a hydroxy group, a fluoro atom, and an amino group, and wherein the carbon chain optionally comprises an additional nitrogen atom, optionally substituted with a $C_{1-3}$ alkyl group, or wherein the carbon chain optionally comprises an additional oxygen atom, sulphur atom, carbonyl group, sulfonyl group, amide group, sulfonamide group, ureido group, or aryl group, wherein the aryl group is optionally substituted with from 1 to 4 substituents chosen from a halogen atom, a cyano group, a methyl group, a methoxy group, a trifluoromethyl group, $OCHF_2$, $OCF_3$, $SCF_3$, and a nitro group;

B is chosen from one of:

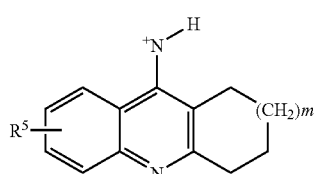
(B¹)

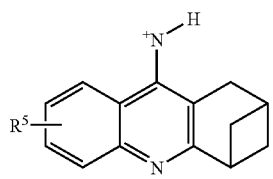
(B²)

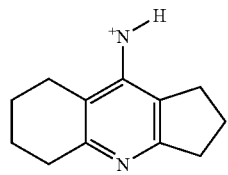
(B³)

wherein the "+" symbol is the position at which one of (B1) to (B3) is connected to T of formula (1), $R^5$ is chosen from a hydrogen atom, a halogen atom, a methoxy group, and a trifluoromethoxy group, and m is 0, 1 or 2; and
 n is 0 or 1.

2. A compound as claimed in claim 1, wherein A is one of:

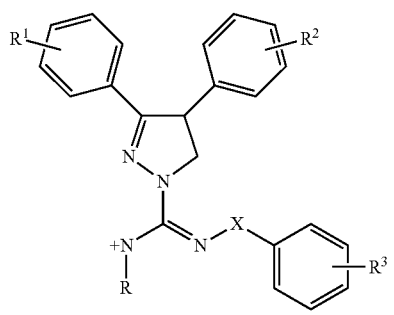
(A¹ᵃ)

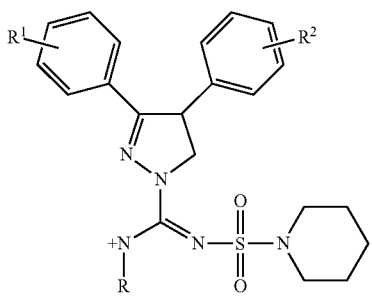
(A¹ᵇ)

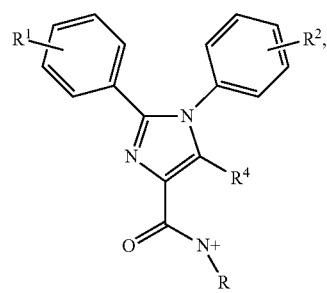
(A²)

n is 1 and B is tacrine:

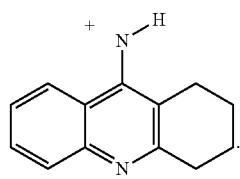

3. A compound as claimed in claim 1, wherein A is one of:

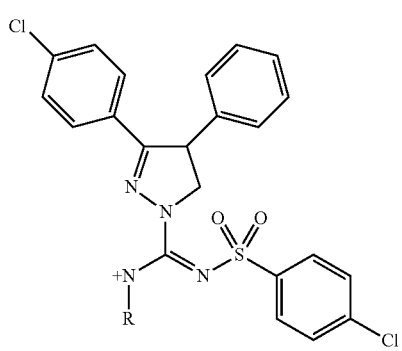
(A⁹)

-continued

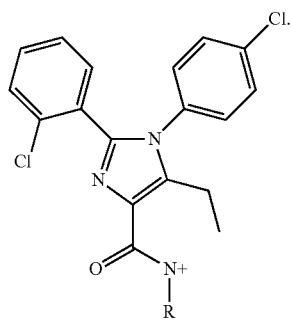

(A¹⁰)

4. A compound as claimed in claim 1, wherein the compound is chosen from:
- 4-chloro-N-{[3-(4-chlorophenyl)-4-phenyl-4, 5-dihydro-1H-pyrazolyl]-[7-(1,2,3,4-tetrahydroacridin-9-ylamino)heptylamino]methylene}benzene-sulfonamide;
- 4-chloro-N-{[3-(4-chlorophenyl)-4-phenyl-4,5-dihydro-1H-pyrazo-lyl]-[7-(1,2,3,4-tetrahydroacridin-9-yl-amino)butylamino]methylene}benzene sulfonamide;
- N-[7-(1,2,3,4-tetrahydroacridin-9-ylamino)heptyl]-2-(2-chlorophenyl)-1-(4-chlorophenyl)-5-ethyl-1H-imidazole-4-carboxamide; and
- N-[4-(1,2,3,4-tetrahydroacridin-9-ylamino)butyl]-2-(2-chlorophenyl)-1-(4-chlorophenyl)-5-ethyl-1H-imidazole-4-carboxamide.

5. A compound as claimed in claim 1, wherein the compound is chosen from:

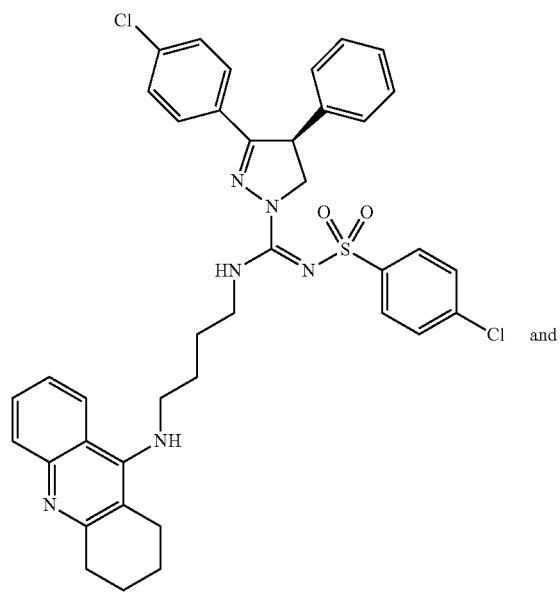

-continued

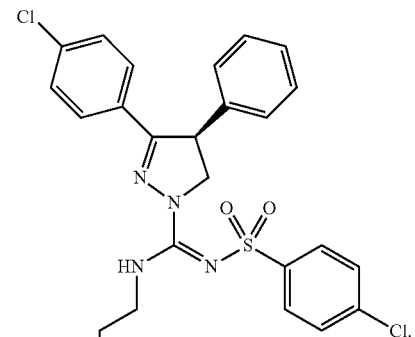

6. A compound as claimed in claim 1, wherein said compound is an optically active enantiomer.

7. A process for preparing a compound of formula (1)

$$A{-}{\left[T\right]}_{n}{-}B \qquad (1)$$

wherein A is chosen from (A¹ᵃ) and (A¹ᵇ)

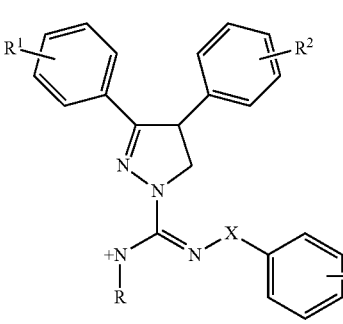

(A¹ᵃ)

-continued

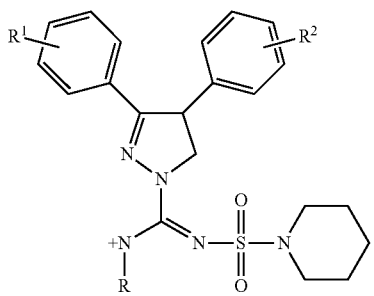
(A$^{1b}$)

wherein each of R$^1$, R$^2$ and R$^3$ is a hydrogen atom, a trifluoromethyl group or a halogen atom, the process comprising:

(1) reacting a compound of (A$^{1a1}$) or (A$^{1b1}$) with a chlorinating agent, in the presence of a base, in an inert organic solvent to yield a compound of formula (A$^{1a2}$) or (A$^{1b2}$), and (2) reacting a compound of formula (A$^{1a2}$) or (A$^{1b2}$) with a compound of formula HRN-T-B, wherein B is tacrine or a tacrine analog, T is chosen from a saturated or unsaturated linear carbon chain having from 2 to 8 carbon atoms, wherein the carbon chain is optionally substituted with from 1 to 5 substituents chosen from a methyl group, an ethyl group, a hydroxy group, a fluoro atom, and an amino group, and wherein the carbon chain optionally comprises an additional nitrogen atom, optionally substituted with a C$_{1-3}$ alkyl group, or wherein the carbon chain optionally comprises an additional oxygen atom, sulphur atom, carbonyl group, sulfonyl group, amide group, sulfonamide group, ureido group, or aryl group, wherein the aryl group is optionally substituted with from 1 to 4 substituents chosen from a halogen atom, a cyano group, a methyl group, a methoxy group, a trifluoromethyl group, OCHF$_2$, OCF$_3$, SCF$_3$, and a nitro group, and R is a hydrogen atom or a C$_{1-3}$ alkyl group

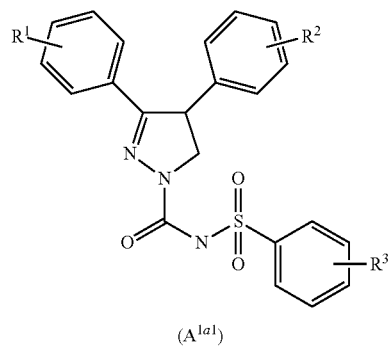
(A$^{1a1}$)

—chlorinating agent / base→

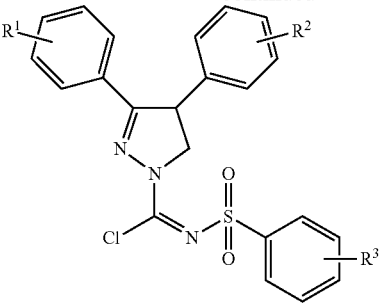
(A$^{1a2}$)

HRN-T-B →

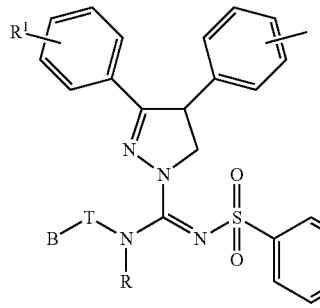
(1)

—chlorinating agent / base→

(A$^{1b1}$)

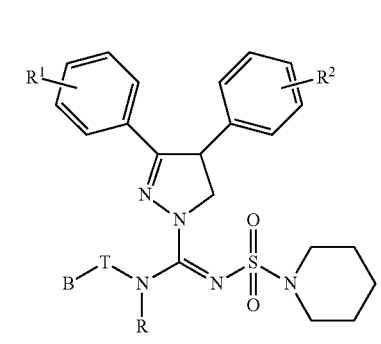
(A$^{1b2}$)

HRN-T-B →

(1)

8. A compound prepared according to the process recited in claim 7.

9. A medicament comprising a compound of formula (1):

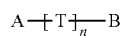

(1)

or a tautomer, stereoisomer, N-oxide, or a pharmacologically acceptable salt of any of the foregoing, wherein:

A is chosen from one of:

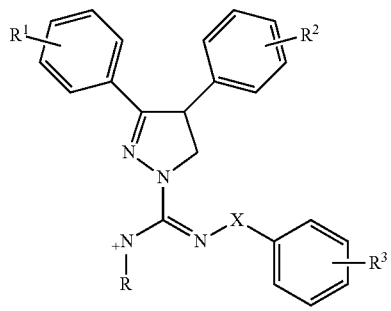

($A^{1a}$)

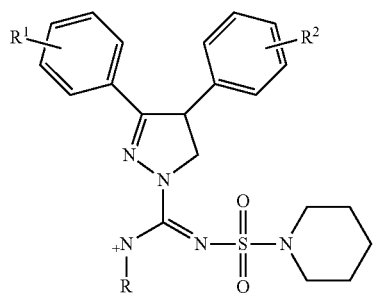

($A^{1b}$)

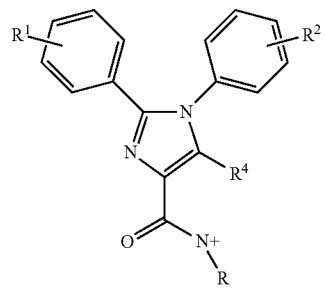

($A^2$)

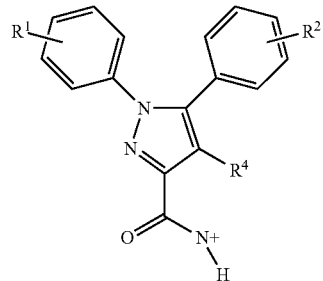

($A^3$)

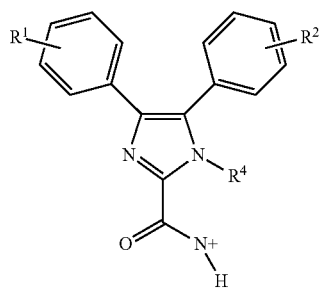

($A^4$)

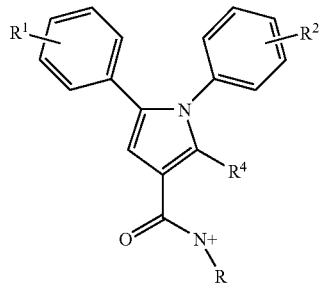

($A^5$)

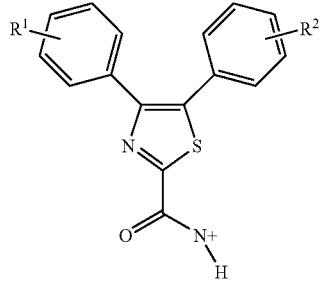

($A^6$)

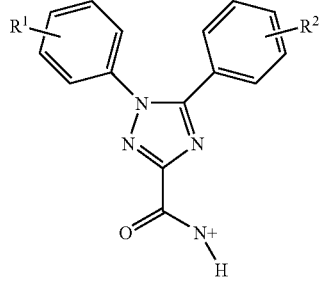

($A^7$)

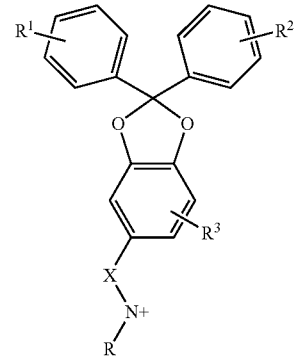

($A^8$)

wherein X is a sulfonyl or a carbonyl group, the sign + is the position at which one of ($A^{1a}$) to ($A^8$) is connected to T of formula (1), each of $R^1$, $R^2$ and $R^3$ is chosen from a hydrogen atom, a trifluoromethyl group, and a halogen atom, $R_4$ is chosen from a hydrogen atom, a halogen atom, a methyl group, an ethyl group, a trifluoromethyl group, a hydroxymethyl group, a fluoromethyl group, a 2,2,2-trifluoroethyl group, a propyl group, a methylsulfanyl group, a methylsulfinyl group, a methylsulfonyl group, an ethylsulfanyl group, an ethylsulfinyl group, an ethylsulfonyl group, a $C_{1-3}$-dialkylaminomethyl group, a pyrrolidin-1-ylmethyl group, a piperidin-1-ylmethyl group, and a morpholin-4-ylmethyl group, and R is a hydrogen atom or a $C_{1-3}$ alkyl group;

T is chosen from a saturated or unsaturated linear carbon chain having from 2 to 8 carbon atoms, wherein the carbon chain is optionally substituted with from 1 to 5 substituents chosen from a methyl group, an ethyl group, a hydroxy group, a fluoro atom, and an amino group, and wherein the carbon chain optionally comprises an additional nitrogen atom, optionally substituted with a $C_{1-3}$ alkyl group, or wherein the carbon chain optionally comprises an additional oxygen atom, sulphur atom, carbonyl group, sulfonyl group, amide group, sulfonamide group, ureido group, or aryl group, wherein the aryl group is optionally substituted with from 1 to 4 substituents chosen from a halogen atom, a cyano group, a methyl group, a methoxy group, a trifluoromethyl group, $OCHF_2$, $OCF_3$, $SCF_3$, and a nitro group;

B is chosen from one of:

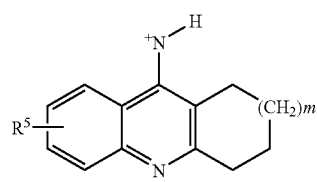

(B¹)

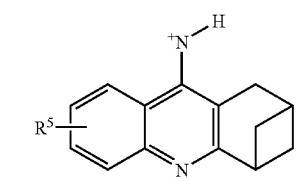

(B²)

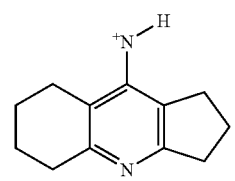

(B³)

wherein the "+" symbol is the position at which one of (B1) to (B3) is connected to T of formula (1), $R^5$ is chosen from a hydrogen atom, a halogen atom, a methoxy group, and a trifluoromethoxy group, and m is 0, 1 or 2; and n is 0 or 1.

10. A pharmaceutical composition comprising, at least one pharmaceutically acceptable carrier, at least one pharmaceutically acceptable auxiliary substance, or a combination of two or more thereof; and a therapeutically acceptable amount of at least one compound of formula (1):

(1)

or a tautomer, stereoisomer, N-oxide, or a pharmacologically acceptable salt of any of the foregoing, wherein:

A is chosen from one of:

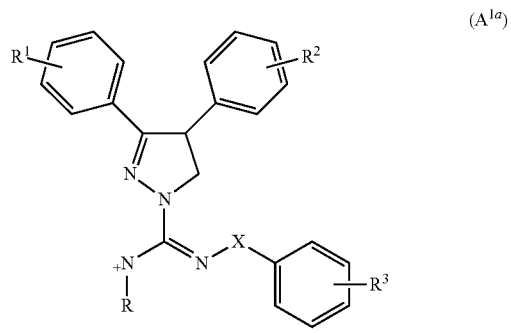

(A¹ᵃ)

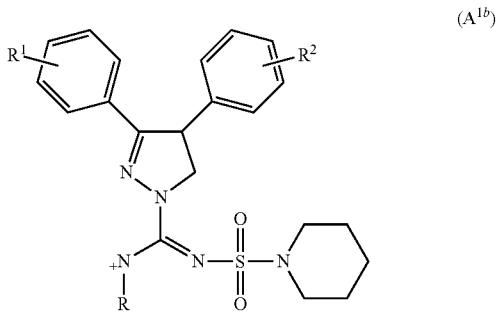

(A¹ᵇ)

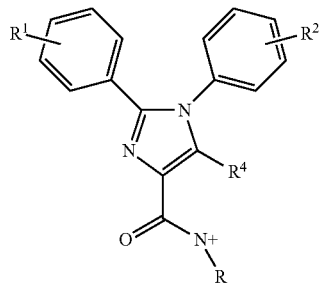

(A²)

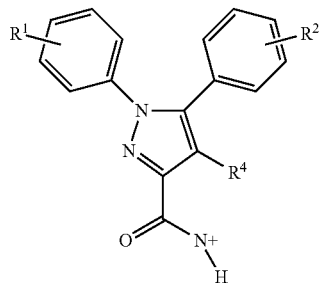

(A³)

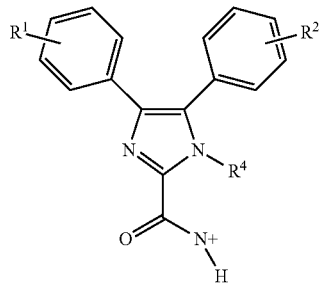

(A⁴)

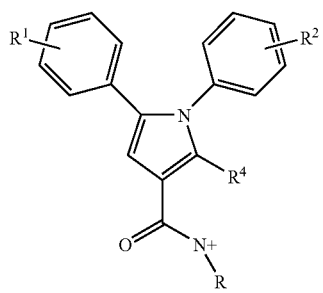
(A⁵)

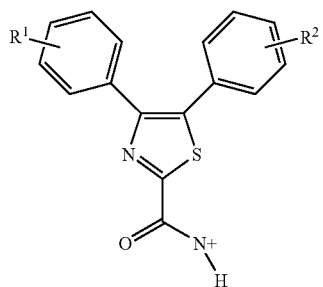
(A⁶)

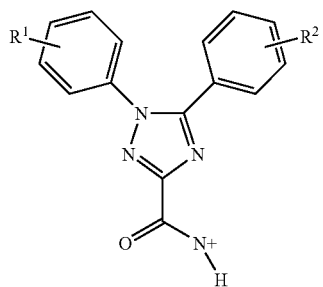
(A⁷)

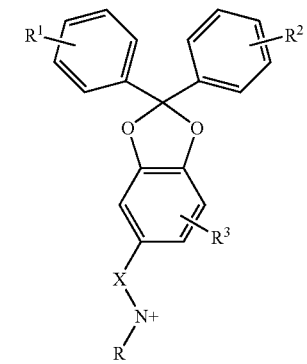
(A⁸)

wherein X is a sulfonyl or a carbonyl group, the skin + is the position at which one of (A¹ᵃ) to (A⁸) is connected to T of formula (1), each of R¹, R² and R³ is chosen from a hydrogen atom a trifluoromethyl group, and a halogen atom R₄ is chosen from a hydrogen atom, a halogen atom, a methyl group, an ethyl group, a trifluoromethyl group, a hydroxymethyl group, a fluoromethyl group, a 2,2,2-trifluoroethyl group, a propyl group, a methylsulfanyl group, a methylsulfinyl group, a methylsulfonyl group, an ethylsulfanyl group, an ethylsulfinyl group, an ethylsulfonyl group, a $C_{1-3}$-dialkyl-aminomethyl group, a pyrrolidin-1-ylmethyl group, a piperidin-1-ylmethyl group, and a morpholin-4-ylmethyl group, and R is a hydrogen atom or a $C_{1-3}$ alkyl group;

T is chosen from a saturated or unsaturated linear carbon chain having from 2 to 8 carbon atoms, wherein the carbon chain is optionally substituted with from 1 to 5 substituents chosen from a methyl group, an ethyl group, a hydroxy group, a fluoro atom, and an amino group, and wherein the carbon chain optionally comprises an additional nitrogen atom, optionally substituted with a $C_{1-3}$ alkyl group, or wherein the carbon chain optionally comprises an additional oxygen atom, sulphur atom, carbonyl group, sulfonyl group, amide group, sulfonamide group, ureido group, or aryl group, wherein the aryl group is optionally substituted with from 1 to 4 substituents chosen from a halogen atom, a cyano group, a methyl group, a methoxy group, a trifluoromethyl group, $OCHF_2$, $OCF_3$, $SCF_3$, and a nitro group;

B is chosen from one of:

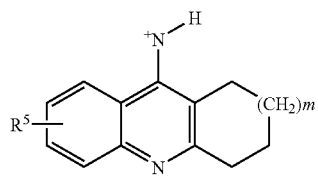
(B¹)

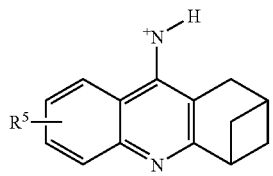
(B²)

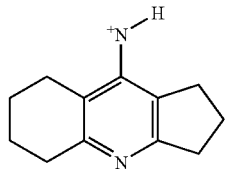
(B³)

wherein the "+" symbol is the position at which one of (B1) to (B3) is connected to T of formula (1), R⁵ is chosen from a hydrogen atom, a halogen atom, a methoxy group, and a trifluoromethoxy group, and m is 0, 1 or 2; and n is 0 or 1.

11. A method of treating at least one condition chosen from Alzheimer's disease, cognitive disorders, memory disorders, dementia, traumatic brain injury, drug dependence and addiction, the method comprising administering a therapeutically effective amount of a composition comprising a compound of formula (1), to a mammal in need thereof, wherein formula (1) is $$A\text{---}(T)_n\text{---}B \qquad (1)$$

or a tautomer, stereoisomer, N-oxide, or a pharmacologically acceptable salt of any of the foregoing, wherein:

A is chosen from one of:

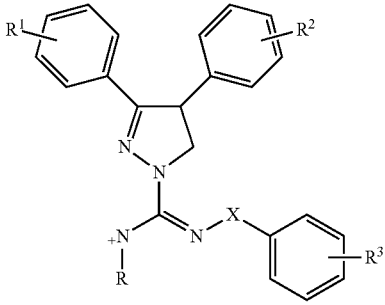
(A¹ᵃ)

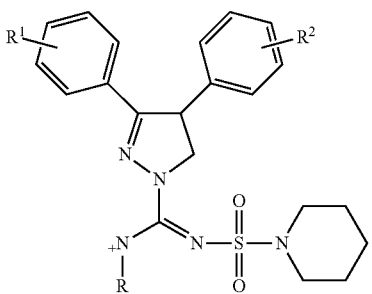
(A¹ᵇ)

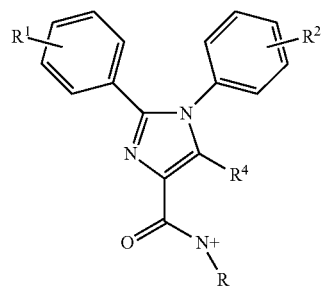
(A²)

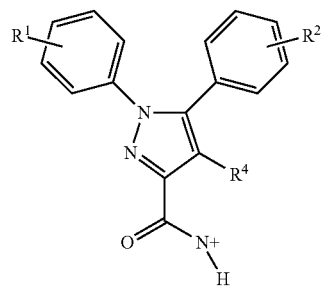
(A³)

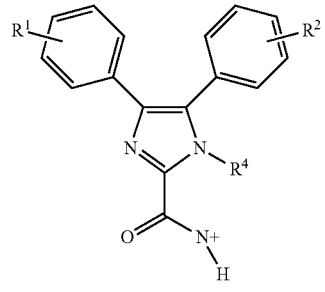
(A⁴)

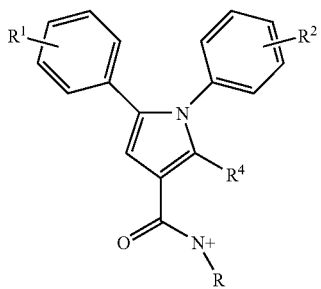
(A⁵)

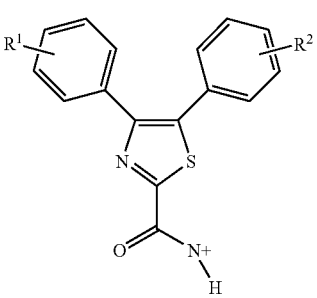
(A⁶)

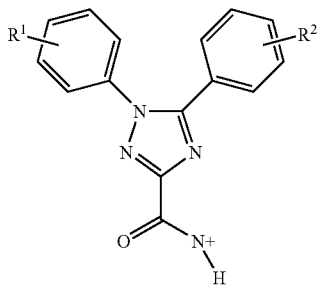
(A⁷)

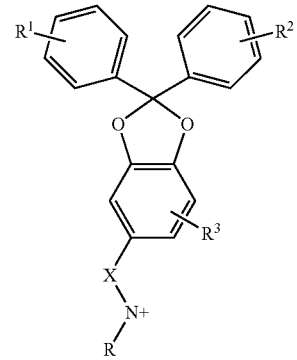
(A⁸)

wherein X is a sulfonyl or a carbonyl group, the sign + is the position at which one of ($A^{1a}$) to ($A^8$) is connected to T of formula (1), each of $R^1$, $R^2$ and $R^3$ is chosen from a hydrogen atom, a trifluoromethyl group, and a halogen atom, $R_4$ is chosen from a hydrogen atom, a halogen atom, a methyl group, an ethyl group, a trifluoromethyl group, a hydroxymethyl group, a fluoromethyl group, a 2,2,2-trifluoroethyl group, a propyl group, a methylsulfanyl group, a methylsulfinyl group, a methylsulfonyl group, an ethylsulfanyl group, an ethylsulfinyl group, an ethylsulfonyl group, a $C_{1-3}$-dialkylaminomethyl group, a pyrrolidin-1-ylmethyl group, a piperidin-1-ylmethyl group, and a morpholin-4-ylmethyl group, and R is a hydrogen atom or a $C_{1-3}$ alkyl group;

T is chosen from a saturated or unsaturated linear carbon chain having from 2 to 8 carbon atoms, wherein the carbon chain is optionally substituted with from 1 to 5 substituents chosen from a methyl group, an ethyl group, a hydroxy group, a fluoro atom, and an amino group, and wherein the carbon chain optionally comprises an additional nitro en atom optionally substituted with a $C_{1-3}$ alkyl group, or wherein the carbon chain optionally comprises an additional oxygen atom, sulphur atom, carbonyl group, sulfonyl group, amide group, sulfonamide group, ureido group, or aryl group, wherein the aryl group is optionally substituted with from 1 to 4 substituents chosen from a halogen atom, a cyano group, a methyl group, a methoxy group, a trifluoromethyl group, $OCHF_2$, $OCF_3$, $SCF_3$, and a nitro group;

B is chosen from one of:

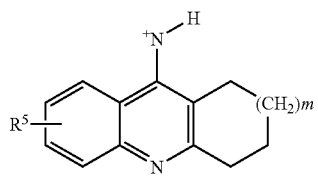
(B$^1$)

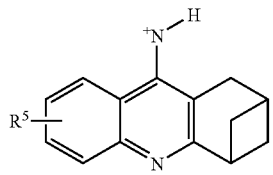
(B$^2$)

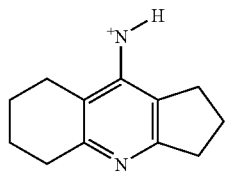
(B$^3$)

wherein the "+" symbol is the position at which one of (B1) to (B3) is connected to T of formula (1), $R^5$ is chosen from a hydrogen atom, a halogen atom, a methoxy group, and a trifluoromethoxy group, and m is 0, 1 or 2; and n is 0 or 1.

* * * * *

UNITED STATES PATENT AND TRADEMARK OFFICE
CERTIFICATE OF CORRECTION

PATENT NO.         : 8,063,062 B2
APPLICATION NO.    : 11/957948
DATED              : November 22, 2011
INVENTOR(S)        : Josephus H. M. Lange et al.

It is certified that error appears in the above-identified patent and that said Letters Patent is hereby corrected as shown below:

Claim 5, col. 42, lines 27-30, delete " [chemical structure] ".

Claim 9, col. 47, line 8, "piperidin-1-vlmethyl" should read -- piperidin-1-ylmethyl --.*

Claim 9, col. 47, line 50, "symbolis" should read -- symbol is --.

Claim 11, col. 53, line 5, "nitro en atom" should read -- nitrogen atom --.*

Signed and Sealed this
Twenty-eighth Day of August, 2012

David J. Kappos
*Director of the United States Patent and Trademark Office*